(12) United States Patent
Donnelly

(10) Patent No.: US 7,083,960 B2
(45) Date of Patent: Aug. 1, 2006

(54) **PRODUCTION OF A HIGHLY ACTIVE, SOLUBLE FORM OF THE CYTOCHROME P450 REDUCTASE (CPR A) FROM *CANDIDA TROPICALIS***

(75) Inventor: Mark Donnelly, Warrenville, IL (US)

(73) Assignee: Cognis Corporation, Ambler, PA (US)

( * ) Notice: Subject to any disclaimer, the term of this patent is extended or adjusted under 35 U.S.C. 154(b) by 251 days.

(21) Appl. No.: 10/272,017

(22) Filed: Oct. 15, 2002

(65) Prior Publication Data

US 2003/0119145 A1 Jun. 26, 2003

Related U.S. Application Data

(60) Provisional application No. 60/328,752, filed on Oct. 12, 2001.

(51) Int. Cl.
| | |
|---|---|
| *C12N 9/02* | (2006.01) |
| *C12N 1/20* | (2006.01) |
| *C12N 15/00* | (2006.01) |
| *C12M 5/00* | (2006.01) |
| *C12P 21/04* | (2006.01) |
| *C12Q 1/00* | (2006.01) |
| *C07H 21/04* | (2006.01) |

(52) U.S. Cl. ............ 435/189; 435/252.3; 435/320.1; 435/69.1; 435/71.1; 435/4; 435/6; 435/325; 435/440; 536/23.2; 536/23.7

(58) Field of Classification Search ............ 435/189, 435/440, 6, 252.3, 320.1, 254.1, 254.22, 435/252.33, 4, 69.1, 71.1, 325; 536/23.2, 536/23.1, 23.7; 530/350
See application file for complete search history.

(56) References Cited

U.S. PATENT DOCUMENTS 6,331,420 B1 * 12/2001 Wilson et al. ............... 435/145

FOREIGN PATENT DOCUMENTS

WO WO 00/20566 4/2000

OTHER PUBLICATIONS

Sutter et al. Isolation and characterization of the alkane-inducible NADPH-cytochrome P-450 oxidoreductase gene from *Candida tropicalis*. Identification of invariant residues within similar amino acid sequences of divergent flavoporteins.*
Sutter et al. NCBI Accession No. P37201-1994.*
Shi et al. Effects of sequential deletions of residues from the N- or C-terminus on the functions of epsilon subunit of the chloroplast ATP synthase. Biochemistry. Sep. 11, 2001;40(36):10825-31.*

(Continued)

*Primary Examiner*—P. Achutamurthy
*Assistant Examiner*—Yong D. Pak
(74) *Attorney, Agent, or Firm*—John F. Daniels

(57) ABSTRACT

The present invention provides soluble cytochrome p450 reductase (CPR) proteins from *Candida* sp. having an altered N-terminal region which results in reduced hydrophobicity of the N-terminal region. Also provided are host cells comprising the subject soluble CPR proteins. In addition, the present invention provides nucleotide and corresponding amino acid sequences for soluble CPR proteins and vectors comprising the nucleotide sequences. Methods for producing a soluble CPR, for increasing production of a dicarboxylic acid, and for detecting a cytochrome P450 are also provided.

39 Claims, 10 Drawing Sheets

OTHER PUBLICATIONS

Muller et al. A 36-residue peptide contains all of the information required for 7B2-mediated activation of prohormone convertas 2. J Biol Chem. Jul. 23, 1999;274(30):21471-7.*

Ron et al. Expression of biologically active recombinant keratinocyte growth factor. Structure/function analysis of amino-termin truncation mutants. J Biol Chem. Feb. 5, 1993;268(4):2984-8.*

Trevino et al. Truncations at the NH2 terminus of rhodanese destabilize the enzyme and decrease its heterologous expression J Biol Chem. Oct. 23, 1998;273(43):27841-7.*

Smith et al. Dissection of NADPH-cytochrome P450 oxidoreductase into distinct functional domains. Proc Natl Acad Sci U S A Aug. 30, 1994;91(18):8710-4.*

Sequence Alignment—SEQ ID No.:83 of Wilson et al. and SEQ ID No.:2 of instant invention.*

Lamb et al. (1999) "Generation of a Complete, Soluble, and Catalytically Active Sterol 14α-Demethylase-Reductase Complex" *Biochemistry*, 38(27): 8733-8738.

Lamb et al. (2001) "Activities and Kinetic Mechanisms of Native and Soluble NADPH-Cytochrome P450 Reductase" *Biochemical and Biophysical Research Communications*, 286:48-54.

Venkateswarlu et al. (1998) "The N-Terminal Membrane Domain of Yeast NADPH-Cytochrome P450 (CYP) Oxidoreductase Is Not Required for Catalytic Activity in Sterol Biosynthesis or in Reconstitution of CYP Activity" *The Journal of Biological Chemistry*, 273(8):4492-4496.

Yabusaki et al. (1988) "Genetically Engineered Modification of P450 Monooxygenases: Functional Analysis of the Amino-Terminal Hydrophobic Region and Hinge Region of the P450/Reductase Fused Enzyme", *DNA*, 7(10):701-711.

* cited by examiner

Figure 2

```
 1  MPFGIVNIVFV---------------VLAGLVLAVLLV
 1  MA--LDKLDLY---------------VIITLVVAVAAV
 1  MGDSHEDTSAIMPEAVAEEVSLFSTTDMVLFSLIVGVLTV

24  VKRRSIKELLMSDVGDVTAVSSGN--KVIAQVVTERRKNY
22  FAKNQF--LDQVQDTGFLNVDSGSNSRDVLLTLKKNKNT
41  WFIFRKKKEEIPEFSKIQTTAPPVKESSFVEKMKKTGRNI

62  LVLVASVTGTHEDYHK
60  LLLFGSQTGTAEDYAN
81  IVFYGSQTGTAEEFAN
```

PRODUCTION OF A HIGHLY ACTIVE, SOLUBLE FORM OF THE CYTOCHROME P450 REDUCTASE (CPR A) FROM *CANDIDA TROPICALIS*

CROSS-REFERENCE TO RELATED APPLICATION

This application claims benefit of U.S. Provisional Application No. 60/328,752 filed Oct. 12, 2001, which application is incorporated by reference herein.

STATEMENT REGARDING FEDERALLY SPONSORED RESEARCH OR DEVELOPMENT

This invention was made with Government support under WFO Agreement No. 85J04, Prime Contract No. W-31-109-ENG-38 awarded by the Department of Energy. The United States Government has certain rights in the invention.

BACKGROUND OF THE INVENTION

Cytochrome P450 reductase is part of the ω-hydroxylase enzyme complex that catalyzes the first step in the ω-oxidation pathway. Cytochrome P450 reductase (CPR) catalyzes the reduction of the heme iron of various cytochromes, including cytochrome c and cytochrome P450. CPR has been renamed in recent literature as NADPH:cytochrome P450 oxidoreductase (NCP). The present application however, refers to the enzyme by its older designation, CPR. In the case of cytochrome P450s, this reduction initiates the catalytic steps that activate oxygen and result ultimately in the oxidation of substrates. In *C. tropicalis*, one class of cytochrome P450s catalyzes the ω-hydroxylation of fatty acids and the α,ω-hydroxylation of alkanes. Subsequent reactions by other enzymes generate α,ω-dicarboxylic acids, which are useful as raw materials for the preparation of numerous products such as perfumes, polymers, adhesives, coatings, lubricants, and macrolid antibiotics.

Cytochrome P450s are heme thiolate proteins consisting of a heme moiety bound to a single polypeptide chain of 45,000 to 55,000 daltons (Da). The iron of the heme prosthetic group is located at the center of a protoporphyrin ring. Four ligands of the heme iron can be attributed to the porphyrin ring. The fifth ligand is a thiolate anion from a cysteinyl residue of the polypeptide. The sixth ligand is probably a hydroxyl group from an amino acid residue, or a moiety with a similar field strength such as a water molecule as described, e.g., in Goeptar et al., *Critical Reviews in Toxicology* 25(1):25–65 (1995), incorporated herein by reference.

Monooxygenation reactions catalyzed by cytochrome P450 in a eukaryotic membrane-bound system require the transfer of electrons from NADPH to cytochrome P450 via NADPH-cytochrome P450 reductase (CPR) as described, e.g., in Taniguchi et al., *Arch. Biochem. Biophys.* 232:585 (1984), incorporated herein by reference. CPR is a flavoprotein of approximately 78,000 Da containing 1 mol of flavin adenine dinucleotide (FAD) and 1 mol of flavin mononucleotide (FMN) per mole of enzyme as described, e.g., in Potter et al., *J. Biol. Chem.* 258:6906 (1983), incorporated herein by reference. The FAD moiety of CPR is the site of electron entry into the enzyme, whereas FMN is the electron-donating site to cytochrome P450 as described, e.g., in Vermilion et al., *J. Biol. Chem.* 253:8812 (1978), incorporated herein by reference. The overall reaction is as follows:

$$H^+ + RH + NADPH + O_2 \rightarrow ROH + NADP^+ + H_2O$$

Binding of a substrate to the catalytic site of cytochrome P450 apparently results in a conformational change initiating electron transfer from CPR to cytochrome P450. Subsequent to the transfer of the first electron, $O_2$ binds to the $Fe_2^+$-P450 substrate complex to form $Fe_3^+$-P450-substrate complex. This complex is then reduced by a second electron from CPR, or, in some cases, NADH via cytochrome b5 and NADH-cytochrome b5 reductase as described, e.g., in Guengerich et al., *Arch. Biochem. Biophys.* 205:365 (1980), incorporated herein by reference. One atom of this reactive oxygen is introduced into the substrate, while the other is reduced to water. The oxygenated substrate then dissociates, regenerating the oxidized form of the cytochrome P450 as described, e.g., in Klassen, Amdur and Doull, *Casarett and Doull's Toxicology,* Macmillan, New York (1986), incorporated herein by reference.

The natural CPR proteins contain a hydrophobic N-terminal domain that anchors to membranes, resulting in localization of the protein in the microsomal fraction of cells, not in the cytoplasmic fraction that contains freely soluble proteins. A soluble CPR from rat has been produced recombinantly in yeast by Yabusaki et al. 1988, who reported a 33-fold enhancement of activity over the membrane-bound form. When adjusted for the observed 20-fold higher expression of the protein (based on antibody binding) however, the intrinsic enhancement of soluble CPR activity was less than 2-fold. A soluble CPR from *S. cerevisiae* has also been reported by Venkateswarlu et al. 1998. This soluble CPR had approximately the same activity as the microsomal form.

A full length CPR purified from *C. maltosa* in the presence of detergents, has a reported final specific activity of only about 63 U/mg (Scheller et al. 1996). Values reported for full-length CPRs purified from other sources are similar to those for *C. maltosa,* ranging from 50–70 U/mg protein (Dignam and Strobel, 1977; Yasukochi and Masters, 1976). Masters et al. have determined the specific activities of the purified full-length rat liver CPR and its proteolytically solubilized derivative to be almost identical, approximately 60 U/mg (Masters et al., 1975; Yasukochi and Masters, 1976).

The aforementioned activities are for reduction of cytochrome c, not for the oxidation of a substrate in P450-dependent reactions. In the rat and *S. cerevisiae* examples, the soluble CPRs were about 80% as active in reactions coupled to the hydroxylase activity of cytochrome P450s (Lamb et al., 1999; Venkateswarlu et al., 1998; Yabusaki et al., 1988).

Previous work in *Candida tropicalis* has demonstrated that strains genetically engineered to contain multiple copies of a full-length reductase gene, result in increased diacid production. See U.S. Pat. No. 6,331,420. Host cells engineered to produce one or more copies of a soluble form of reductase having activity in cytochrome P450-dependent reactions are highly desirable for several reasons. An enzymatically active, soluble CPR will not compete for space in the membranes, therefore allowing higher production of the membrane associated cytochrome P450s and fatty alcohol oxidase genes. In addition, less stress will be placed on the host cells. The present invention provides compositions and methods related to the production of a highly active, soluble form of cytochrome P450 reductase (CPR) from *Candida tropicalis*.

SUMMARY OF THE INVENTION

The present invention provides a soluble cytochrome P450 reductase (CPR) from *Candida* sp. wherein the CPR has an altered N-terminal region which results in reduced hydrophobicity of the N-terminal region. The CPR molecules of the present invention are capable of complementing a membrane-associated cytochrome P450 anchored in a microsomal membrane. In one embodiment of the invention, a subject CPR lacks all or a part of the N-terminal hydrophobic domain. In another embodiment of the invention, hydrophobic amino acids in the N-terminal region are substituted with hydrophilic amino acids. Examples of soluble CPRs include those comprising an amino acid sequence as set forth in at least one of SEQ ID NO:2, SEQ ID NO:3, SEQ ID NO:5, or SEQ ID NO:6. In the case of a subject CPR having an altered N-terminal region where the translational initiation signal (methionine) is removed, a methionine residue is included before the first amino acid such as before the first amino acid in any of the sequences set forth in SEQ ID Nos 2, 3, 5, or 6.

If desired, a subject CPR further comprises at the N-terminal end, a heterologous peptide sequence such as a purification moiety or secretion sequence. Prokaryotic and eukaryotic host cells comprising a subject CPR are also provided. Examples of prokaryotic cells useful for practicing the present invention include *E. coli* cells. Examples of eukaryotic cells useful for practicing the present invention include yeast, insect, animal, or plant cells.

The present invention also provides Isolated nucleic acid molecules encoding a soluble cytochrome P450 reductase (CPR) wherein the soluble CPR comprises an amino acid sequence as set forth in any one of SEQ ID NOs:2, 3, 5, or 6. Such amino acid sequences may further comprise hydrophilic amino acid residues at the N-terminal end. Examples of such isolated nucleic acid molecules include sequences such as those set forth in SEQ ID NO:1 or SEQ ID NO:4. The present invention also provides vectors comprising a subject nucleic acid molecule. Examples of such vectors include plasmids, phagemids, phage or cosmids. Host cells transfected or transformed with a subject nucleic acid molecule encoding a soluble CPR are also provided.

In another aspect of the invention, there is provided a method for producing a soluble cytochrome P450 reductase (CPR). The method comprises the steps of transforming a suitable host cell with a nucleotide sequence encoding a *Candida* sp. CPR having an altered N-terminal region which results in reduced hydrophobicity of the N-terminal end, wherein the nucleotide sequence is operably linked to a promoter which functions in the host cell and a codon for a translational start signal; and culturing the host cell under conditions favorable for expression of the soluble CPR. If desired, the soluble CPR of the present invention may further comprise a heterologous peptide sequence which enhances secretion of the CPR from the host cell.

In yet another aspect of the invention, there is provided a method for increasing production of a dicarboxylic acid. The method involves (a) providing a host cell having one or more genes for a cytochrome P450;
(b) introducing into the host cell, one or more coding sequences for a *Candida* sp. soluble CPR having an altered N-terminal region which results in reduced hydrophobicity of the N-terminal region, wherein said coding sequence is operatively linked to a promoter which functions in the host cell and a translational initiation codon; and
(c) culturing the host cell under conditions favorable for expression of the soluble CPR.

Still further provided by the present invention is a method for detecting a cytochrome P450. The method comprises:

(a) isolating a microsomal preparation from an organism;
(b) adding a soluble P450 cytochrome reductase (CPR) to the microsomal preparation wherein said soluble CPR comprises the amino acid sequence set forth in SEQ ID NO:2, 3, 5, or 6;
(c) measuring oxidation of NADPH; and
(d) correlating an increase in oxidation of NADPH with the detection of a P450.

A method for producing a carboxylic acid is also provided by the present invention. The method comprises the steps of culturing *Candida* sp. in a fermentation medium containing a substrate of the formula $R(CH_2)nCH_3$, wherein $n=\geq 1$ and R is selected from the group consisting of epoxide, alkoxy, ether, saturated primary alcohol, cyloalky, aryl, diol and diol ester, wherein at least one terminal methyl group of the substrate is oxidized to a carboxylic acid, and wherein the *Candida* sp. expresses one or more copies of a gene for a soluble CPR.

BRIEF DESCRIPTION OF THE SEVERAL VIEWS OF THE DRAWINGS

FIG. 2 is an alignment of purified CPR amino acid sequences from *S. cerevisiae* (upper line, Ref. 2), *C. tropicalis* (middle line, present application) and rat (lower line, Ref. 1). Angle brackets in the $2^{nd}$ row indicate the exemplified truncation point for each protein. The first amino acid after the brackets indicates the beginning of the truncated protein.

DETAILED DESCRIPTION OF THE INVENTION

Figure 1:
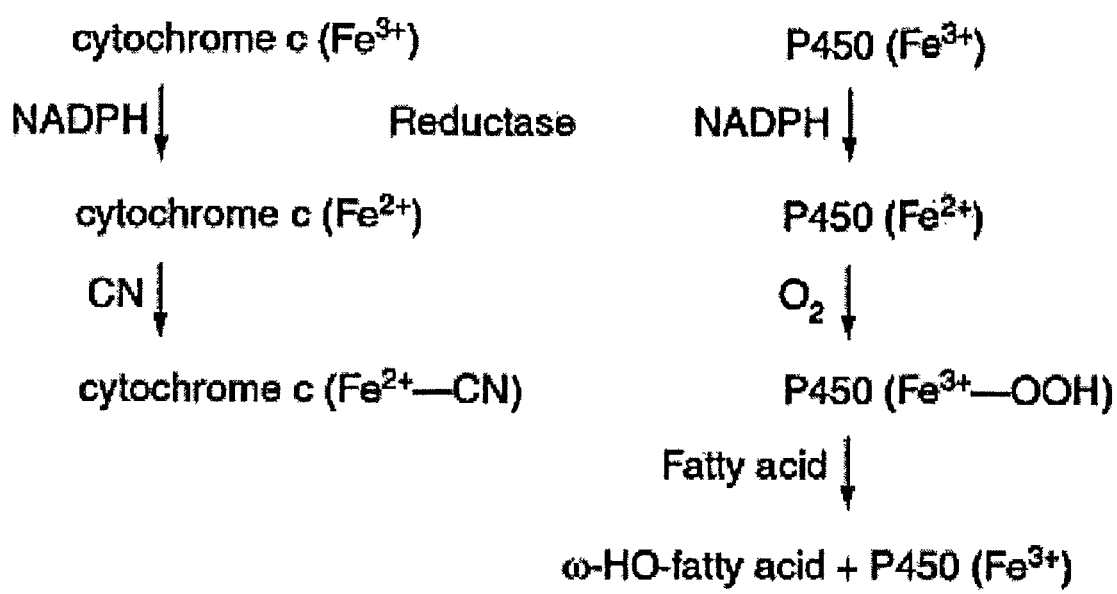
FIG. 1 is a flow chart showing reactions catalyzed by CPR (cytochrome P450 reductase). CPR has been renamed NADPH:cytochrome P450 oxidoreductase (NCP). It catalyzes the first step in ω-hydroxylation, reduction of cytochrome P450 to the $Fe^{2+}$ state. The iron atom then activates oxygen, generating an intermediate that oxidizes fatty acids and alkanes to ω-hydroxyacids and ω-hydroxyalkanes. Activity of CPR (NCP) is often assayed by measuring reduction of the soluble heme protein, cytochrome c, in a step analogous to the reduction of the cytochrome P450s. Interaction of the reduced cytochrome c with cyanide (CN) gives a colored product

In accordance with the present invention, it has been surprisingly found that a soluble form of *Candida tropicalis* CPR produced in Sf9 insect or *E. coli* cells transfected with a truncated CPR A gene exhibits increased activity over previously reported soluble forms of CPR obtained from other organisms.

A comparison of the soluble and membrane associated forms of CPR produced in Sf9 insect cells indicates that production of the soluble form generated approximately 50-fold more activity in these cells. A polyhistidine tagged soluble CPR produced in *E. coli* and purified to homogeneity was 10-fold more active in cytochrome c reduction than purified CPRs from *C. maltosa* and mammalian cells. Both an untagged form of soluble *C. tropicalis* CPR produced in Sf9 insect cells and a purified, tagged form of soluble *C. tropicalis* CPR produced in *E. coli*, also react with membrane-associated, fatty acid-oxidizing cytochrome P450s of *C. tropicalis* in intact membranes to initiate ω-hydroxylation of fatty acids. These results mimic the conditions required for enhancement of hydroxylation in vivo, where a soluble form of CPR would be required to couple to a membrane associated cytochrome P450 without removal of the cytochrome P450 from membranes by solubilization with detergents.

In accordance with the present invention, there is provided a soluble form of *C. tropicalis* CPR protein which can be produced to higher amounts in vivo than the membrane-bound form of the enzyme and which supports reactions catalyzed by cytochrome P450 enzymes still embedded in membranes as occurs in vivo. Complete nucleotide sequences for the A and B alleles of a CPR gene from *C. tropicalis* as well as amino acid sequences for the corresponding CPRA and CPRB proteins are provided in U.S. Pat. No. 6,331,420, the disclosure of which is incorporated by reference herein as if fully set forth.

An exemplified soluble *C. tropicalis* CPRA protein of the present invention has the first 31 amino acids of the N-terminal domain removed as illustrated in FIG. 2. The CRP protein is normally bound to membranes by this N-terminal hydrophobic amino acid sequence. Removal of the first 31 amino acids at the N-terminal end of CPR results in a soluble protein which retains reductase activity.

Other soluble forms of CPR from *Candida* sp. are also contemplated by the present invention. For example, modification of the amino acid sequence at the N-terminus produces changes in secondary or tertiary structure, and result in profound changes in membrane interactions necessary for binding. Such changes may be achieved by approaches evident to one skilled in the art. For example, the amino acid sequence of the N-terminal region could be modified either by removing hydrophobic residues or by removing and replacing them with hydrophilic residues. The first 31 amino acid residues of both CPRA and CPRB have the following sequence:

M-A-L-D-K-L-D-L-Y-V-I-I-T-L-V-V-A-V-A-A-Y-F-A-K-N-Q-F-L-D-Q-P

Of these 31 amino acid residues, 17 are considered to be hydrophobic, including alanine (A), leucine (L), isoleucine (I), valine (V) and threonine (T). The sequence contains 5 charged amino acids including aspartic acid (D) and lysine (K). Fifteen of the first 20 amino acids are hydrophobic. Decreased hydrophobicity may be achieved by replacing one or more of the hydrophobic amino acid residues with amino acids such as histidine, tryptophan, proline, phenylalanine, glutamine, serine, tyrosine, asparagine, glutamic acid, aspartic acid, lysine or arginine. A decrease in hydrophobicity results in a loss of membrane binding. Decreased hydrophobicity (increased solubility) could also result from a shortening of the N-terminal region, in particular the removal of one or more of the 15 hydrophobic amino acids comprising the first 20 residues. An increase in the number of charged amino acids may also modify membrane binding by making the molecule less hydrophobic.

Since CPRs are known to reduce many different cytochrome P450s, a soluble CPR of the present invention is useful as a general reagent in bioassays involving many different cytochrome P450s. A soluble CPR of the present invention is useful in aiding in the discovery and characterization of P450s from diverse organisms. For example, a soluble CPR of the present invention may be added to a microsomal preparation obtained from a different organism. The corresponding cytochrome P450 may be detected by and its reactions products characterized. For example, cytochrome P450 may be detected by measuring oxidation of NADPH in a spectrophotometric assay. Alternatively, a substrate may be labeled, e.g., lauric acid, and the labeled product, ω-hydroxy lauric acid, detected. A method for measuring the activity of cytochrome P450 activity is described in detail in the literature e.g., Tsotsou, G. E., et al. (2002), the disclosure of which is incorporated by reference herein as if fully set forth. Because a soluble CPR protein can be produced readily in *E. coli* cells with a polyhistidine leader sequence, it can be purified easily for use as a reagent for the evaluation of various cytochrome P450s of the reduction of other heme-containing proteins.

A soluble CPR of the present invention may be synthesized chemically using any of the well known methods of protein synthesis. A soluble CPR of the present invention may also be produced recombinantly using a coding sequence for a CPR having an altered N-terminal sequence such as a truncated sequence or a sequence having amino acid residue substitutions.

In another embodiment of the invention, there are provided isolated nucleic acid molecules comprising a nucleotide sequence encoding a soluble *Candida* sp. CPR wherein the N-terminal membrane-binding domain of the enzyme is altered as described herein. Such alterations can include removal of all or a part of the hydrophobic N-terminal region of the protein, resulting in a less hydrophobic molecule which is not membrane bound. For example, all or a part of the coding sequence corresponding to the first 31 amino acids in the N-terminal region of a CPR may be removed. Alternatively, as described above, coding sequence corresponding to substitution of hydrophilic amino acids for hydrophobic amino acids in the N-terminal end of the protein may also be made. The skilled artisan is adept at altering a *CPR* gene such as e.g., designing a corresponding coding sequence having all or a part of the hydrophobic N-terminal region removed or altered as described above. All alterations to a CPR protein or *CPR* gene which result in decreased hydrophobicity of a CPR molecule are encompassed by the present invention so long as such alterations are sufficient to significantly reduce and/or eliminate association of a CPR with a membrane and which therefore result in a soluble CPR.

In accordance with the present invention, there is provided a subject nucleotide sequence encoding a soluble protein having an amino acid sequence as set forth in SEQ ID NO:2. An example of such an isolated nucleotide sequence is set forth in SEQ ID NO:1, which nucleotide sequence corresponds to the A allele of *CPR* (*CPRA*).

It has recently been determined that certain eukaryotes, e.g., certain yeast, do not adhere, in some respects, to the "universal" genetic code which provides that particular codons (triplets of nucleic acids) code for specific amino acids. Indeed, the genetic code is "universal" because it is virtually the same in all living organisms. Certain *Candida* sp. are now known to translate the CTG codon (which, according to the "universal" code designates leucine) as serine. See, e.g., Ueda et al., *Biochemie* (1994) 76, 1217–1222, where *C. tropicalis, C. cylindracea, C. guilliermodii* and *C. lusitaniae* are shown to adhere to the "non-universal" code with respect to the CTG codon. Accordingly, nucleic acid sequences may code for one amino acid sequence in "universal" code organisms and a variant of that amino acid sequence in "non-universal" code organisms depending on the number of CTG codons present in the nucleic acid coding sequence. The difference may become evident when, in the course of genetic engineering, a nucleic acid molecule encoding a protein is transferred from a "non-universal" code organism to a "universal" code organism or vice versa. Obviously, there will be a different amino acid sequence depending on which organism is used to express the protein.

Thus, the present invention also provides an amino acid sequence (set forth in SEQ ID NO:3) for a soluble CPR when said CPR is expressed in a species of *Candida* such as *C. tropicalis.*

In another embodiment of the invention, there is provided a nucleotide sequence encoding a soluble protein having an amino acid sequence as set forth in SEQ ID NO:5. An example of such an isolated nucleotide sequence is set forth in SEQ ID NO:4, which nucleotide sequence corresponds to the B allele of CPR (CPRB). In addition, an amino acid sequence for a CPR is set forth in SEQ ID NO:6 when said CPR is expressed in a species of *Candida* such as *C. tropicalis.* A small number of additional amino acids may be further removed from the soluble CPRs described herein and still retain reductase activity. A skilled artisan is able to make such additional deletions and test for activities employing no more than routine procedures described herein and/or in the literature extant.

When a nucleotide sequence encoding a soluble CPR is a truncated or altered sequence and is to be expressed in a host cell, a translational initiation codon such as methionine, is preferably added just after the sequence corresponding to the altered N terminal end, i.e., just before the initial codon for glutamine (Gln) in SEQ ID NO:2, to ensure proper initiation of translation. For example, a methionine codon may be added just before nucleotide 1 of the sequence set forth in SEQ ID NO:1. In addition to a methionine codon, there are other nucleotide sequences which may be added upstream (5') to coding sequence corresponding to the N terminal end of a soluble CPR of the present invention. Such nucleotide sequences and the corresponding peptide sequences are heterologous with respect to a CPR gene. For example, sequence for a purification moiety such as a his-tag may be added to the N-terminal end of a truncated CPR gene. The polyhistidine leader sequence of the form expressed in *E. coli* allows easy purification of the protein (FIG. 5), and allows economical production of soluble CPR.

An example of a his-tag is: M H H H H H H S S G L V P R G S H M. There are various expression vectors available having coding sequence for a his-tag, e.g., pET15b (Novagen), and pProEX-1 (Life technologies). If desired, the his-tag may be removed after isolation of the subject CPR protein by digesion with a specific protease. See Hochuli et al. (1998).

Coding sequences for peptides which enhance secretion of a soluble CPR protein from the host cell may also be added to the 5' end of the coding sequence for a truncated CPR. Examples of peptides which enhance secretion of proteins include the ompA leader sequence for secretion from *E. coli* (Skerra et al. (1991) and signal peptides from extracellular enzymes such as proteases, amylases, cellulases, xylenases, and lipases.

In yet another embodiment of the invention, there are provided host cells transfected with the isolated nucleic acid molecules encoding a soluble *C. tropicalis* CPR. For expression of the CPR in the host cell, preferably, a subject isolated nucleic acid molecule is inserted into a vector. Accordingly, the present invention also provides vectors comprising a coding sequence for a soluble *C. tropicalis* CPRA having an altered N-terminal domain. Preferably, the coding sequence for a soluble CPRA having an altered N-terminal domain such as the exemplified truncated CPRA protein, further comprises a methionine codon as a first codon and is operatively linked to a promoter which is capable of expressing the truncated CPR in the host cell. Host cells may be prokaryotic and/or eukaryotic. Examples of prokaryotic cells include bacterial cells such as *E. coli, Bacillus* sp. and *Streptomyces* sp. Examples of eukaryotic cells include fungal cells such as yeast, insect cells such as *Drosophila* S2 and *Spodoptera* Sf9, plant or animal cells. The selection of an appropriate host is deemed to be within the scope of those skilled in the art from the teachings herein and can include those *Candida* host strains described in U.S. Pat. No. 6,331,420, the disclosure of which is incorporated by reference herein as if fully set forth.

Depending on the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_r$ and $P_L$ promoters of coliphage lambda and others, including but not limited to lacUV5, ompF, bla, lpp, and the like, may be used to direct high levels of transcription of adjacent DNA segments. Additionally, a hybrid trp-lacUV5(tac) promoter or other *E. coli* promoters produced by recombinant DNA or other synthetic DNA techniques may be used to provide for transcription of the inserted soluble CPR gene.

When insect cells are used as host cells, promoters from different viruses which infect insect cells may be used, such as for example, promoters from Baculovirus, and densoviruses such as *Aedes aegypti,* and *Ades albopictus*. The polH promoter from Baculovirus may also be used.

In accordance with the present invention, an appropriate host cell is chosen depending on the intended use of the subject CPR protein. For example, purified soluble CPR for use as a general reagent in bioassays involving different cytochrome P450s, may be conveniently produced in insect or bacterial cells.

The soluble CPR of the present invention may also be produced in yeast cells in order to increase diacid production. In a preferred embodiment, the host cell is from the yeast *Candida*. In a more preferred embodiment, the host cell is *Candida tropicalis*. When a coding sequence for a soluble CPR gene is used to transfect a yeast cell of the genus *Candida,* a promoter from *Candida* sp. is preferably used. Even more preferably, the host cell is *Candida tropicalis*. Examples of promoters which by be used to control expression of a truncated CPR gene in *Candida tropicalis* include e.g., those identified in U.S. Pat. No. 6,331,420 such as from the cytochrome P450 monooxygenase genes, CYP52A1, CYP52A2, and CYP52A5. A suitable promoter may also be a CYP52A2A promoter disclosed in copending U.S. patent application Ser. No. 09/911,781, the disclosure of which is incorporated by reference herein as if fully set forth. Alternatively, a soluble CPRA or CPRB gene may be operably linked to its respective native CPRA or CPRB gene promoter. *C. tropicalis* promoters such as the POX4 or POX5 gene promoters may also be used as well as suitable other promoters from *C. tropicalis* or other species of *Candida*.

In accordance with the present invention, soluble CPR proteins may be prepared by methods familiar to those skilled in the art such as by cloning the gene encoding a CPR with an altered or truncated N-terminal domain, e.g., cloning a nucleotide sequence encoding the CPRA protein having the amino acid sequence set forth in SEQ ID NO:2, into an appropriate expression vector followed by expression in a suitable host cell. A methionine codon should be added before the first nucleotide of a sequence encoding the CPRA having the amino acid sequence set forth in SEQ ID NO:2 to ensure proper translational initiation.

The soluble CPR of the present invention may also be generated by direct amplification of corresponding coding sequence via PCR, followed by standard recombinant procedures and expression in a suitable host cell. Primers for use in PCR may be synthetic oligonucleotides prepared on a automated oligonucleotide synthesizer such as an ABI DNA synthesizer available from Perkin-Elmer Corporation. In addition, oligonucleotides may be purchased from commercial manufacturers, for example, from Synthetic Genetics (San Diego, Calif.).

The appropriate DNA sequence may be inserted into an expression vector by a variety of procedures deemed to be within the scope of those skilled in the art, which can include insertion of the DNA into an appropriate restriction endonuclease site(s) or cloning the DNA sequence into the expression vectors using high fidelity polymerase chain reaction. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or tetracycline or ampicillin resistance in *E. coli*.

The vector containing the appropriate DNA sequence as hereinabove described, as well as an appropriate promoter or control sequence, may be employed to transform an appropriate host to permit the host to express the enzyme. "Transformation" includes all forms of causing uptake of foreign DNA by a host cell. The transformed cells are then screened for those which contain the desired DNA and the successful transformants are cultured under conditions which affect the expression of the coding sequences.

It should be understood that host cells into which one or more copies of a desired soluble CPR gene have been introduced can be made to include such a gene by any technique known to those skilled in the art. Suitable host cells include prokaryotes such as *Bacillus* sp., *Pseudomous* sp., *Actinomycetes* sp., *Eschericia* sp., *Mycobacterium* sp., and eukaryotes such as yeast, algae, insect cells, plant cells and filamentous fungi. Suitable host cells are preferably yeast cells such as *Yarrowia, Bebaromyces, Saccharomyces, Schizosaccharomyces, Pichia, Lipomyces, Rhodosporidium, Rhodotorula, Trichosporan, Cryptococcus, Endomyces, Galactomyces, Williopsis, Waltomyces,* and most preferably those of the *Candida* genus. Preferred species of *Candida* are *tropicalis, maltosa, apicola, paratropicalis, albicans, cloacae, guillermondii, intermedia, lipolytica, parapsilosis, viswanathii,* and *zeylenoides.* Preferred hosts include *C. tropicalis* strains that are partially or completely blocked for β-oxidation. Particularly preferred hosts have been genetically modified so that one or more of the chromosomal POX4A, POX4B and both POX5 genes have been disrupted as described e.g., in U.S. Pat. Nos. 5,254,466 and 5,620,878, each incorporated herein by reference. The POX4 and POX5 gene disruptions effectively block the β-oxidation pathway at its first reaction (which is catalyzed by acyl-CoA oxidase) in a *C. tropicalis* host strain. The POX4A and POX5 genes encode distinct subunits of long chain acyl-CoA oxidase, which are the peroxisomal polypeptides (PXPs) designated PXP-4 and PXP-5, respectively. The disruption of one or more of these genes results in a partial or complete inactivation of the β-oxidation pathway thus allowing enhanced yields of dicarboxylic acid by redirecting the substrate toward the ω-oxidation pathway and also prevents reutilization of the dicarboxylic acid products through the β-oxidation pathway.

Examples of strains of *C. tropicalis* which are partially beta-oxidation blocked include, H41, H41B, H51, H45, H43, H53, H534, H534B and H435 as described in aforementioned U.S. Pat. No. 5,254,466. An example of a completely beta-oxidation blocked strain of *C. tropicalis* wherein all four POX4 and POX5 genes are disrupted by a URA3 selectable marker, is H5343 (ATCC 20962) as described in U.S. Pat. No. 5,254,466. Another preferred *C. tropicalis* strain is HDC100, which is described in provisional patent application No. 60/383,332, the disclosure of which is incorporated by reference herein as if fully set forth.

Vectors such as plasmids, phagemids, phages, cosmids, yeast artificial chromosomes, yeast episomal plasmids, yeast replicative plasmids, and the like can be used to transform or transfect suitable host cells. Host cells may also be transformed by introducing into a cell a linear DNA vector(s) containing the desired gene sequence, i.e., a truncated CPR gene. Such linear DNA may be advantageous when it is desirable to avoid introduction of non-native (foreign) DNA into the cell. For example, DNA consisting of a soluble *CPR* gene flanked by DNA sequences which are native to the originating cell can be introduced into the host cell by electroporation, lithium acetate transformation, spheroplasting and the like. Flanking DNA sequences can include selectable markers and/or other tools for genetic engineering. Yeast cells may be transformed with any of the expression vectors described herein. The term "expression vector" is used broadly herein and is intended to encompass any medium which can be used to transform a target cell. Expression vector encompasses all the examples of vectors listed herein, including, for example, integration vectors.

In order to isolate the soluble CPR of the present invention produced in a host cell, cells transformed or transfected with an above-described vector may be disrupted by physical or chemical means known to those skilled in the art, centrifuged, and the resulting crude extract retained for further purification. If a secretion signal is linked to the truncated CPR, the soluble CPR may be isolated from the culture media using standard protocols such as centrifugation followed by ammonium sulfate precipitation of supernatant proteins, and purification processes such as chromatography and electrophoresis.

Purification of a soluble CPR of the present invention may be carried out by any means known to those skilled in the art and can include chromatographic techniques, including immobilized metal affinity chromatography (IMAC) such as nickel affinity chromatography. Commercially available kits for this purification can be purchased from vendors (Qiagen, Inc. Chatsworth, Calif.; Novagen, Calif., USA). An immunoassay, such as a Western blot assay, can then be utilized to verify the presence of the recombinant enzyme using an antibody which specifically binds C. tropicalis CPR. The present invention also provides a method for producing a soluble CPR. The method comprises the steps of: (i) transforming a suitable host cell with a nucleotide sequence encoding a soluble CPR having an altered N-terminal domain which results in reduced hydrophobicity, wherein the nucleotide sequence is operably linked to a promoter which functions in the host cell and a codon for a translational start signal; and (ii) culturing the host cell under conditions favorable for the expression of soluble CPR protein. If desired, the host cells may be mechanically or chemically lysed and the soluble CPR isolated from the lysed cells. Preferably, the coding sequence for a Candida tropicalis soluble CPR having an altered N-terminal domain encodes a truncated protein having an amino acid sequence as set forth in SEQ ID NO:2 or 3. More preferably, the coding sequence for a Candida tropicalis soluble CPR having an altered N-terminal domain comprises the nucleotide sequence set forth in SEQ ID NO:1. In another preferred embodiment, coding sequence for a Candida tropicalis soluble CPR having an altered N-terminal domain encodes a truncated protein having an amino acid sequence as set forth in SEQ ID NO:5 or 6. More preferably, the coding sequence for a Candida tropicalis soluble CPR having an altered N-terminal domain comprises the nucleotide sequence set forth in SEQ ID NO:4.

Where the soluble CPR comprises a his-tag, purification of the soluble CPR may be accomplished by immobilized metal affinity chromatography (IMAC) such as nickel affinity chromatography as described above.

Also provided by the present invention is a method for increasing production of a dicarboxylic acid. The method comprises the steps of providing a host cell having one or more genes for a cytochrome P450, introducing into the host cell one or more coding sequences for a Candida troplicalis soluble CPR wherein the nucleotide sequence is operatively linked to a promoter which functions in the host cell and can express the soluble CPR, as well as a translational initiation codon, and culturing the host cells under conditions favorable for production of the soluble CPR. Preferably, the coding sequence for a Candida tropicalis soluble CPR encodes a truncated protein having an amino acid sequence as set forth any one of SEQ ID NOs:2, 3, 5, or 6. More preferably, the coding sequence for a Candida tropicalis soluble CPR comprises the nucleotide sequence set forth in SEQ ID NO:1 or SEQ ID NO:4. In accordance with the present invention, the above-described method may be performed in host cells already comprising one or more genes for a microsomal CPR.

The soluble CPR in C. troplicalis of the present invention is useful for increasing any cytochrome P450-catalyzed oxidation in yeast cells. For example, as described in copending U.S. patent application Ser. No. 09/812,308, the disclosure of which is incorporated by reference herein as if fully set forth, processes for producing a carboxylic acid by culturing a Candida sp. in a fermentation medium containing substrates other than those described hereinbefore, which substrates require cytochrome P450s, may benefit from expression of a soluble CPR. Examples of such substrates include those of the formula R(CH2)nCH3, wherein $n = \geq 1$ and R is selected from the group consisting of epoxide, alkoxy, ether, saturated primary alcohol, cyloalky, aryl, diol and diol ester. The present invention therefore also provides a method for producing a carboxylic acid comprising culturing Candida sp. in a fermentation medium containing a substrate of the formula R(CH2)nCH3, wherein $n = \geq 1$ and R is selected from the group consisting of epoxide, alkoxy, ether, saturated primary alcohol, cyloalky, aryl, diol and diol ester, wherein at least one terminal methyl group of the substrate is oxidized to a carboxylic acid, and wherein the Candida sp. expresses one or more copies of a gene for a soluble CPR.

The following examples further illustrate the invention.

EXAMPLE 1

Elimination of the Hydrophobic N-terminal Domain of C. tropicalis CPRA

Figure 3:
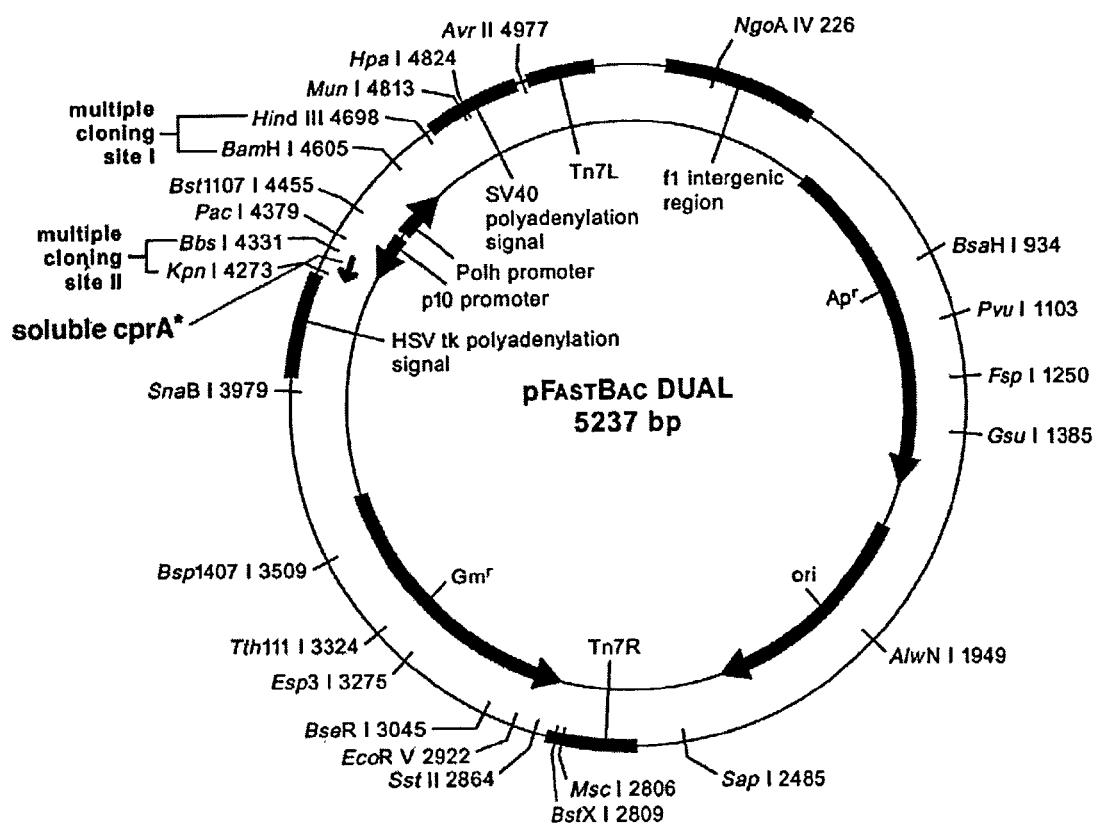
FIG. 3 is a map for the expression vector pFastBAC DUAL, used to produce soluble CPR in Sf9 insect cells.
Figure 4:
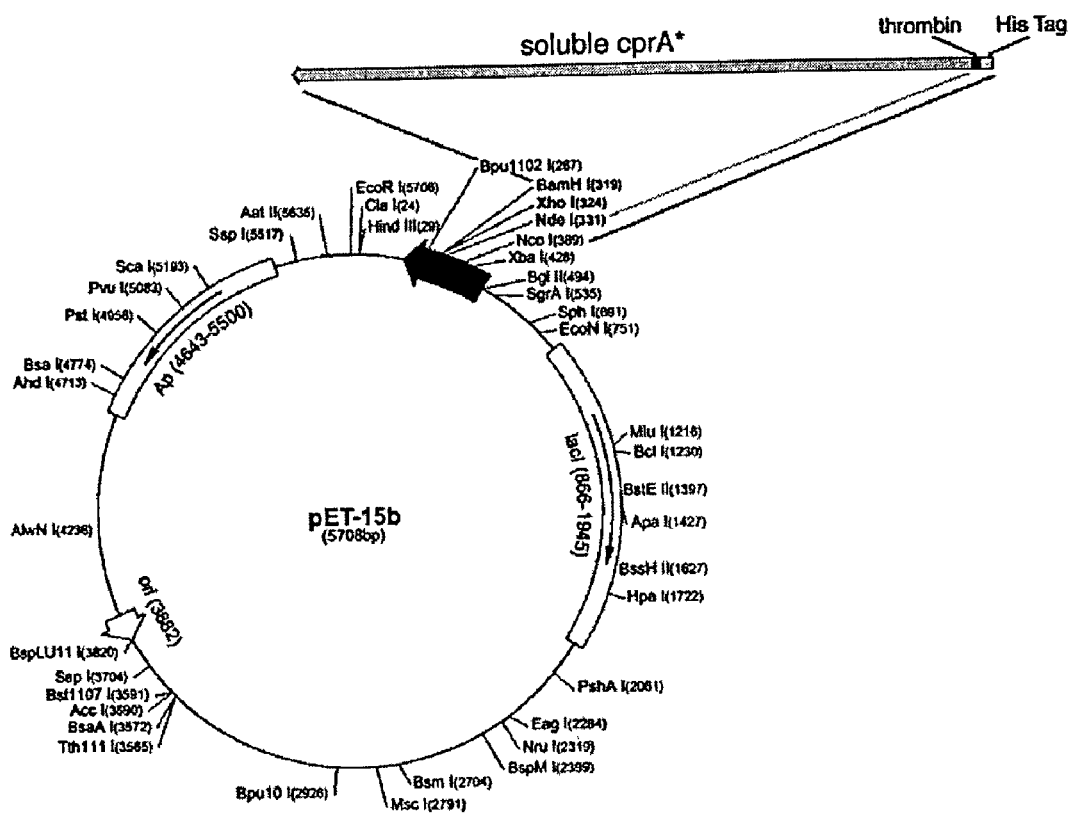
FIG. 4 is a map of the expression vector pET-15b, used to produce the truncated CPR in *E. coli* cells.

The hydrophobic domain of NADPH-cytochrome P450 reductase (CPR) from C. tropicalis was removed via PCR-based modification of the C. tropicalis gene, CPRA, which encodes CPR. Comparison of the amino acid sequence of the C. tropicalis CPR with yeast and mammalian CPRs that have been truncated successfully (Lamb et al., 1999; Venkateswarlu et al., 1998; Yabusaki et al., 1988) identified the N-terminal hydrophobic domain and the amino acid sequence connecting it to the hydrophilic portion exposed to the cytoplasm (FIG. 2). Several PCR steps were required to generate an appropriate form of the gene to express both the full-length and truncated forms of CPR. Primers (Table 1) were designed to (i) change a CTG codon to a serine encoding codon to correct for non-conventional interpretation of the CTG codon in C. tropicalis (Hara et al., 2000; Ueda et al., 1994), (ii) allow expression of the full length CPR in Sf9 insect cells via the Baculovirus cloning system (GibcoBRL), and (iii) generate a truncated form of the gene starting with nucleotides encoding residue 32 for introduction into Baculovirus and E. coli expression vectors. Primers 159U23 and 3029L32 generated one portion of the corrected gene, primers 150L23 and 991U32 to generate the other (Table 1). The template DNA was C. tropicalis genomic DNA. These primers also changed the CTG codon and generated overlapping fragments of the gene. The fragments were combined with the two cloning primers in a PCR to generate the full length, corrected gene by overlap extension PCR (Ho et al., 1989). The truncated CPR gene was generated using the cloned full-length gene as template and primers cprsolU and cprsolL. Both genes were introduced into the Baculovirus expression vector pFastBacDUAL (FIG. 3, Table 2). The product generated by cprsolU and cprsolL (Table 1) was also cloned into the E. coli expression vector pET15b (FIG. 4, Table 2). This vector also adds a polyhistidine leader sequence to the N-terminal of the protein to facilitate its purification. In addition, the gene encoding C. tropicalis ω-hydroxylating cytochrome P450, CYP52A5A, was cloned for expression in the Sf9 insect cells. In this case primers were designed to correct two CTG codons (Table 1). Two overlap extension reactions then generated the full-length, modified gene. The CYP gene was cloned alone into the vector pFastBac1 and with the full-length CPR gene into pFastBacDual.

All PCRs were performed using a Robocycler Gradient 96 thermal cycler (Stratagene) and Platinum pfx DNA polymerase (Life Technologies). Annealing conditions were optimized for each pair of primers and ranged from 51–58° C. at Magnesium concentrations of 1–2 mM. Extension was performed at 72° C. and denaturation at 94° C. 25 to 35 cycles generated products in sufficient yield to allow cloning of the products. Correction of the CTG genes required amplification of fragments of the genes that overlapped in the region that contained the CTG codons. The full-length genes were constructed from these fragment by overlap extension PCR (Ho et al., 1989). All final cloned genes were sequenced in their entirety and confirmed to be correct. The expression clones generated are listed in Table 2.

Genes cloned into the Baculovirus based vectors were introduced into Sf9 cells and the heterologous proteins were expressed using standard protocols. (GibcoBRL; Hood et al., 1997).

Insect cells were harvested by centrifugation at 1000×g for 10 minutes and the cell pellets were frozen at −80° C. Cell pellets were homogenized using a glass Teflon tissue homogenizer in cold resuspension buffer (0.1 M $K_2HPO_4$, pH. 7.4, supplemented with 20% v/v glycerol, 1 mM EDTA and 1 mM glutathione). After removal of cellular debris by centrifugation at 7500 rpm at 4 C for 30 minutes, microsomes were pelleted by centrifugation at 100,000×g for 10 min in a Beckman TL 100 ultracentrifuge. The supernatant fraction contained soluble proteins, including the soluble CPR if it was produced by that cell line. The microsomes were resuspended in resuspension buffer and homogenized. The microsomoal fraction contained the full-length, membrane associated CPRA if it was produced in those cells. Preparations were aliquoted and frozen at −80° C. All the steps of the procedure were carried out at 4° C.

Figure 5:
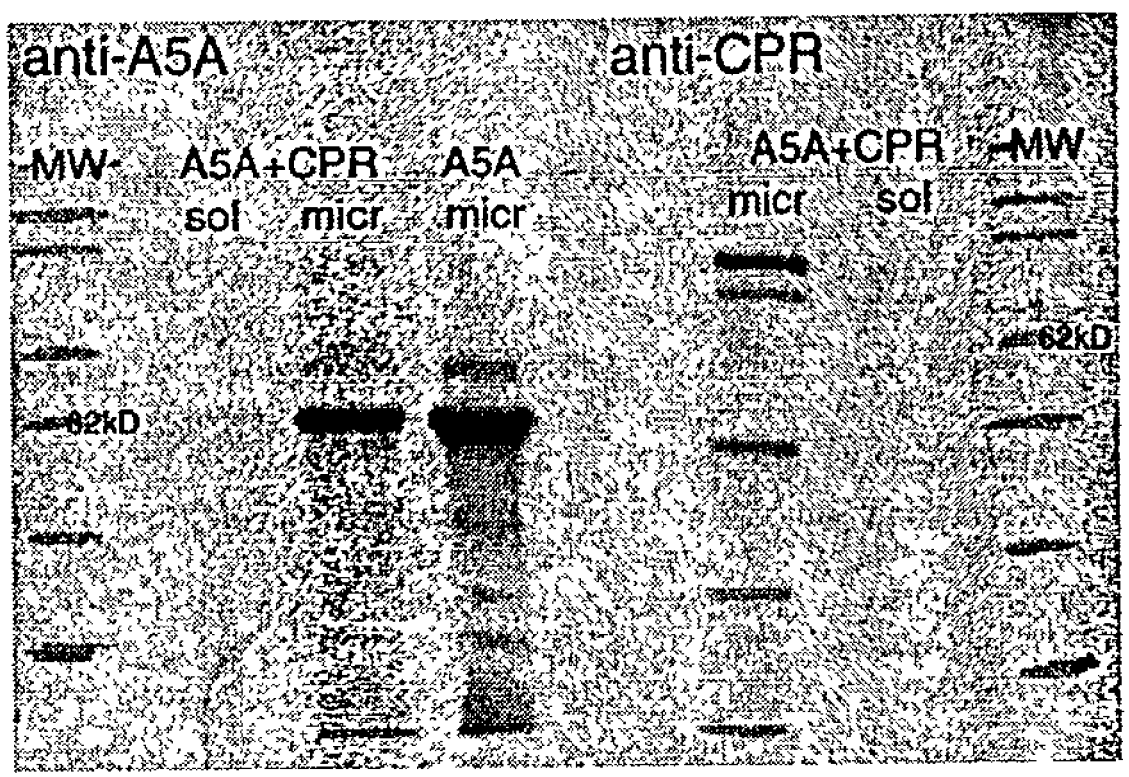
FIG. 5 is a Western analysis of microsomes of Sf9 insect cells containing vectors expressing the full length cytochrome P450 monooxygenase (CYP) and NADPH cytochrome P450 oxidoreductase (CPR) genes. Specific antibodies bind either to CYP52A5A protein or to CPR, which appear as intense bands on gel.
Figure 6:
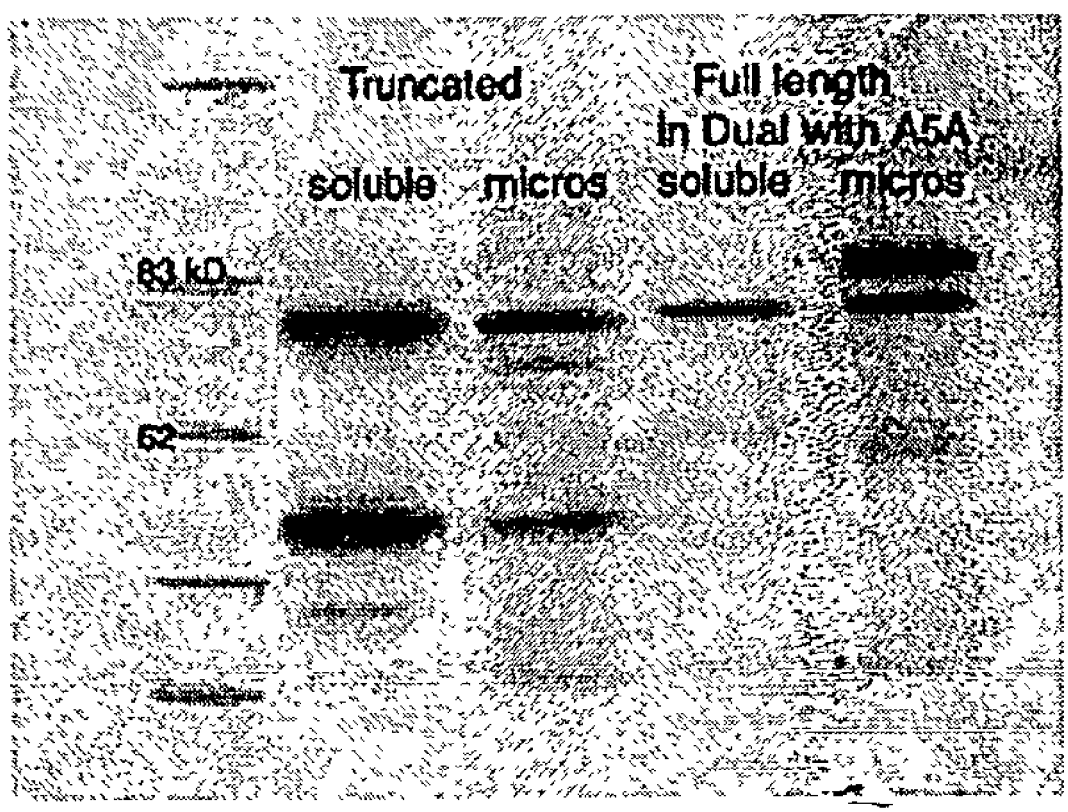
FIG. 6 is a Western analysis of expressed soluble and native CPR in SF9 insect cells. The content of CPR in both soluble (cytoplasmic) and microsomal (micros) fractions are shown. The CPR antibody binds both membrane-bound and soluble CPR.

Western analysis using standard protocols of microsomal fractions and anti-A5A and anti-CPR antibodies revealed expression of both the cytochrome P450s and the reductase (FIG. 5). In contrast, when the truncated reductase gene was expressed in Sf9 cells, the protein was found in the soluble fraction, not in the microsomal fraction (FIG. 6).). A description of the preparation of antibodies to CYP52A5A and CPR may be found in provisional patent application Ser. No. 60/374,066, the disclosure of which is incorporated by reference herein as if fully set forth.

EXAMPLE 2

Activity of Soluble CPR

Activity of the reductase protein was measured by reduction of cytochrome c (Honeck et al., 1982). The assay contained a stock reaction mixture of 40 mM potassium phosphate, pH 7.5, 32 mM nicotinamide and 50 μM cytochrome c. The one milliliter reaction mixture contained 810 μl of the stock reaction mixture, 225 μM sodium cyanide, and 75 μM NADPH. The mixture was equilibrated to 25° C., and enzyme was added to the reaction mixture in a 5–10 μl volume to start the reaction. The $A_{550}$ was monitored using a Cary 1G UV-Visible Spectrophotometer. The Cary Kinetics Application was used to calculate the change in absorbance over a one minute period with 0.1 second interval readings. The correction factor calculated for the data at 550 nm using an extinction coefficient of 21 $mM^{-1}$ $cm^{-1}$ (Honeck et al., 1982).

Enzymatic activity was found in the membrane fraction of cells expressing the full-length CPR and also in the soluble fraction of cells expressing the truncated form (Table 3). The specific activity observed in the Sf9 insect cells expressing the soluble form was approximately 20-fold greater than in the microsomes of cells expressing the unmodified CPR. The increased activity in the microsomal fraction of cells expressing the soluble form most likely reflects contamination of the microsomes with a small amount of cytosolic proteins. The enhanced activity could be due to better production of the protein, higher intrinsic activity of the enzyme, or a combination of both. The nearly equivalent amount of CPR protein in fractions of Sf9 insect cells expressing either the truncated (soluble) or full length (microsomal) protein and detected by Western analysis with anti-CPR antibody (FIG. 6) indicates that the increase was due at least in part to intrinsically higher activity of the enzyme. The amount of protein that reacted with the antibody in the highly active, soluble fraction was only a few fold greater than that in the microsomal fraction containing the unmodified CPR. However, the presence of multiple bands in both the soluble and microsomal fractions makes precise estimates impossible.

To confirm the apparent higher activity of the soluble form, the protein was expressed in E. coli and purified to homogeneity by metal-chelate affinity chromatography (Hochuli et al., 1988). A 50 ml culture of BL21(DE3) cells containing plasmids pLysS and the pET15b vector containing the soluble CPR gene was grown at 30° C. with aeration until an $OD_{600}$ of 0.3–0.5. IPTG was added to the culture to a final concentration of 0.5 mM to induce expression of the soluble CPR. The culture continued to grow for five to six hours at 30° C. with aeration. The cells were collected and the cell pellet was washed with cold 1×TE Buffer pH=7.5. The pellet was stored at −80° C.

The frozen cells were thawed and resuspended in 2.5 ml of 50 mM $NaH_2PO_4$, pH 8.0, 300 mM NaCl, 20 mM imidazole, and 0.5 mM β-mercaptoethanol. The cells were passed through a French Press twice. The cell lysate was centrifuged at 12,000 rpm for 15 minutes. The cleared lysate was collected and loaded onto a Qiagen Ni-NTA Superflow column. The purification was performed using a FPLC system. The column bed volume was approximately 3 mls. The column was equilibrated with buffer containing 50 mM $NaH_2PO_4$, 300 mM NaCl and 20 mM imidazole pH 8.0, according to manufacturers instruction. The elution from the column was monitored at 280 nm. The sample was loaded using a 2 ml loop. The flow rate was 0.25 milliliters/min during the injection of the sample and continued until the first breakthrough of unbound protein. The flow rate was then increased to 1.0 ml/min until all unbound material was washed out of the column and the $OD_{280}$ was back to baseline. The protein was eluted from the column using a linear 1.66%/min gradient of 50 mM $NaH_2PO_4$, pH 8.0, 300 mM NaCl, 250 mM imidazole. Fractions were collected and assayed for CPR activity by reduction of cytochrome c. Fractions demonstrating CPR activity were pooled and concentrated approximately 10 fold. The concentrated protein was dialyzed in 50 mM Tris/HCl, pH 7.5, 0.5 µM FAD, 0.5 µM FMN, 0.5 mM DTT and 20% glycerol at 4° C. overnight. The dialyzed fractions were aliquoted and snap frozen by dropping the tubes into liquid nitrogen. Protein purity was estimated by SDS PAGE analysis. Protein concentrations were determined using the BioRad protein assay.

Figure 7:
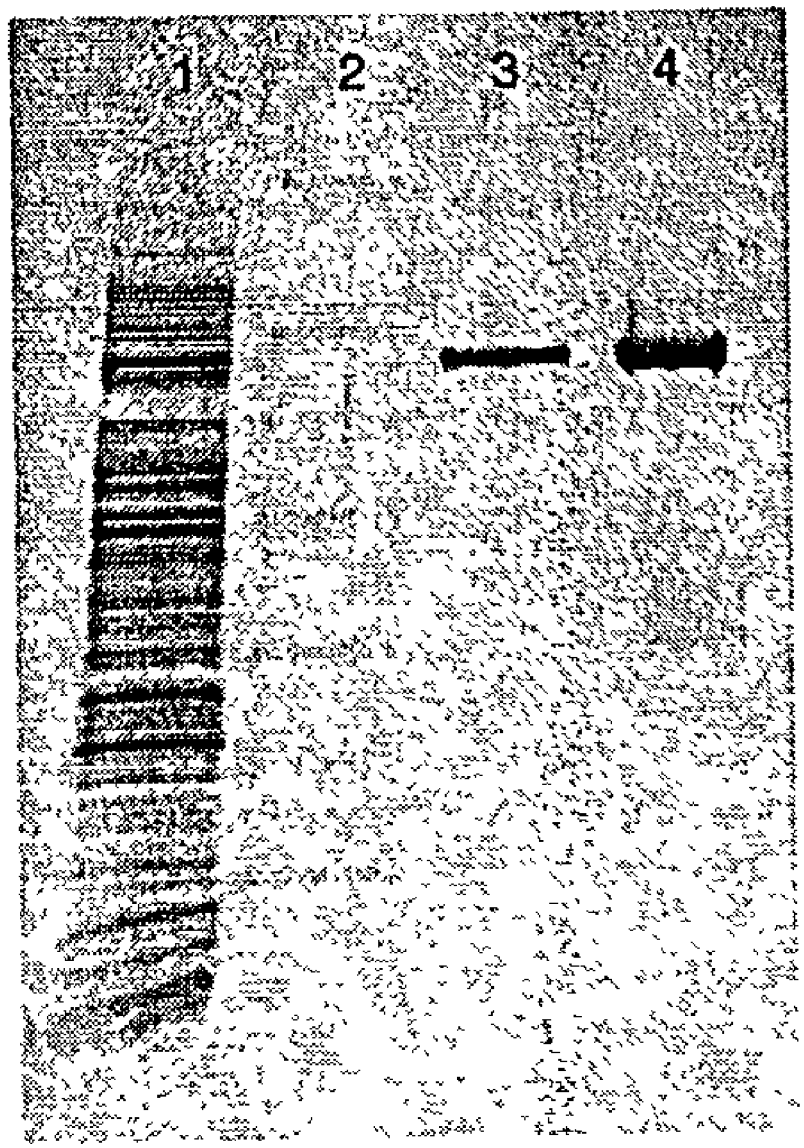
FIG. 7 shows SDS PAGE analysis of the purified his-tagged truncated CPR from *E. coli*. Gel was stained with Commassie Blue. Lanes include, (1) Total soluble proteins, (2) molecular weight markers (6.5, 16.5, 25. 32.5, 47.5, 62, 83, and 117 kDa),(3) purified soluble CPR (4 μg), and (4) purified soluble CPR (30 μg).

The purification gave highly purified, highly active reductase (Table 4, FIG. 7). Only minor contaminants were observed (FIG. 7, lane 4). The final specific activity, 420 units/mg of protein, was nearly 80 fold greater than that observed in the initial lysate (Table 4). Recovery of activity was 44%. Part of the apparent loss of activity is attributed to the presence of unrelated cytochrome c reducing activity in the *E. coli* extracts; the pass through material, which was depleted of the overexpressed reductase, retained significant activity in the assay. However, the enzyme itself clearly is unstable, even in purified, concentrated form. An aliquot of the final preparation was stored overnight at 4° C. and its activity was then compared to the snap frozen enzyme. An additional 30% of the activity was lost during this incubation at 4° C. The frozen enzyme was fully stable.

The results described above indicate that the soluble form of the *C. tropicalis* CPR is much more active than the membrane bound form in the reduction of cytochrome c. Thus, the truncated *C. tropicalis* CPR appears to exhibit an unusual enhancement in activity.

Figure 8:
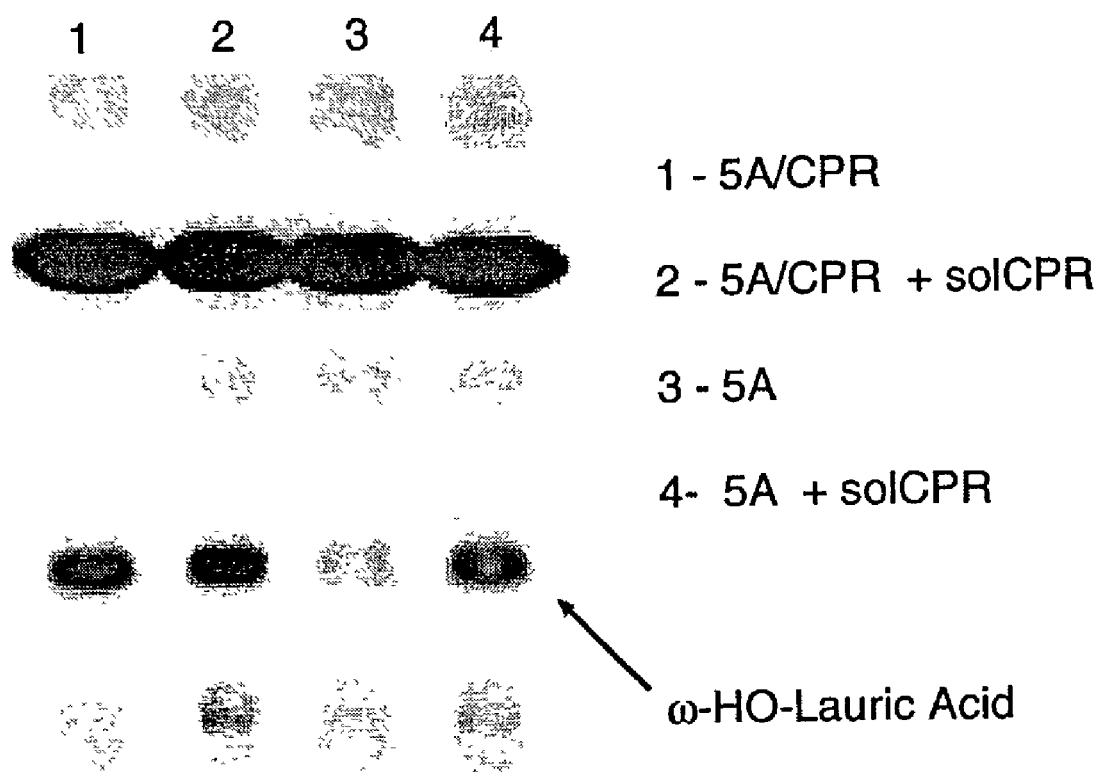
FIG. 8 is an autroradiogram of a TLC plate, showing ω-hydroxylation catalyzed by the soluble CPR of the present invention. Lanes 3 and 4 compare the conversion of [$^{14}$C]-lauric acid by cloned CYP52A5A produced in Sf9 insect cells in the absence (lane 3) and presence (lane 4) of the soluble CPR, present in the supernatant of extracts of Sf9 insect cells expressing the truncated CPRA. Enhancement of formation of ω-hydroxylauric acid was 4.4-fold. In the presence of membrane associated CPR (lanes 1 and 2) addition of the soluble CPR (lane 2) increased ω-hydroxylauric acid formation 6%.

Purification of the enzyme to homogeneity confirmed that the soluble form has higher activity. The specific activity of the purified enzyme produced in *E. coli* was 420 U/mg protein. Although the specific activity of the purified, membrane-bound CPR was not performed, a full length *C. maltosa* CPR, purified in the presence of detergents, had a final specific activity of only 63 U/mg (Scheller et al., 1996). Other full length and soluble CPRs purified from other organisms exhibit similar specific activities (Masters et al. 1975; Yasukochi and Masters, 1976). Thus, all CPRs described in the scientific literature to date, whether soluble or membrane bound, have demonstrated nearly equivalent specific activities. The purified soluble *C. tropicalis* enzyme described herein, however, is approximately 7 times more active than the *C. maltosa* CPR as described supra. The soluble *C. tropicalis* CPR was analyzed for its ability to transfer electrons to the membrane associated *C. tropicalis* cytochrome P450s by assaying the ω-hydroxylation of fatty acids. Microsomal fractions of Sf9 cells that contained either CYP52A5A alone or CYP52A5A in combination with the membrane associated CPRA were incubated with either [$^{14}$C]-lauric acid or myristic acid both with and without addition of the soluble CPR. Paired assay mixtures (250 µl) contained 0.2 M sodium phosphate, pH 7.5, 0.5 mM NADPH, 0.5 mM DTT, 3 mM glucose-6-phosphate, 0.5 U glucose-6-phosphate dehydrogenase and 20 µl microsomes. To one of each pair 7.5 µl of the supernatant fraction containing the soluble CPR (FIG. 6) was also added. [$^{14}$C]-lauric acid (12 nmol, specific activity 57 µCi/µmol) was added and the reactions were incubated at 37° C. with agitation for 1 hour then acidified, extracted into diethyl ether, and analyzed by TLC (FIG. 8). Results were quantified on an InstantImager (Packard Instruments).

The soluble CPR was able to compliment the membrane associated cytochrome P450s effectively, allowing ω-hydroxylation to occur in the absence of coexpressed, membrane bound CPR (FIG. 8, lanes 3 and 4). The small amount of background hydroxylation may be due to the presence of the endogenous CPR of the Sf9 cells weakly complimenting the introduced *C. tropicalis* cytochrome P450. Addition of the soluble CPR increased the hydroxylation activity approximately 5-fold (Table 5). Based on a comparison of the strength of the reaction of the various CPR samples with antibody (FIG. 6), the 7.5 µl of soluble CPR very likely contained considerably less CPR than the 20 µl of microsomes. Titration of the reaction with increasing amounts of CPR will reveal the maximum potential of the protein to compliment the membrane associated cytochrome P450.

Addition of the soluble CPR to membrane preparations that already contained the full-length, membrane associated CPR also increased the ω-hydroxylation, although only moderately (FIG. 8, lanes 1 and 2, and Table 5). These results suggest that while the full potential of the cytochrome P450 for ω-hydroxylation apparently was not obtained with the membrane associated CPR only, addition of the soluble form may only a provide modest increase in ω-hydroxylase activity under these conditions. However, the fact that it does increase the activity suggests that it may be possible fully to activate the cytochrome P450 by addition of the soluble CPR.

Figure 9:
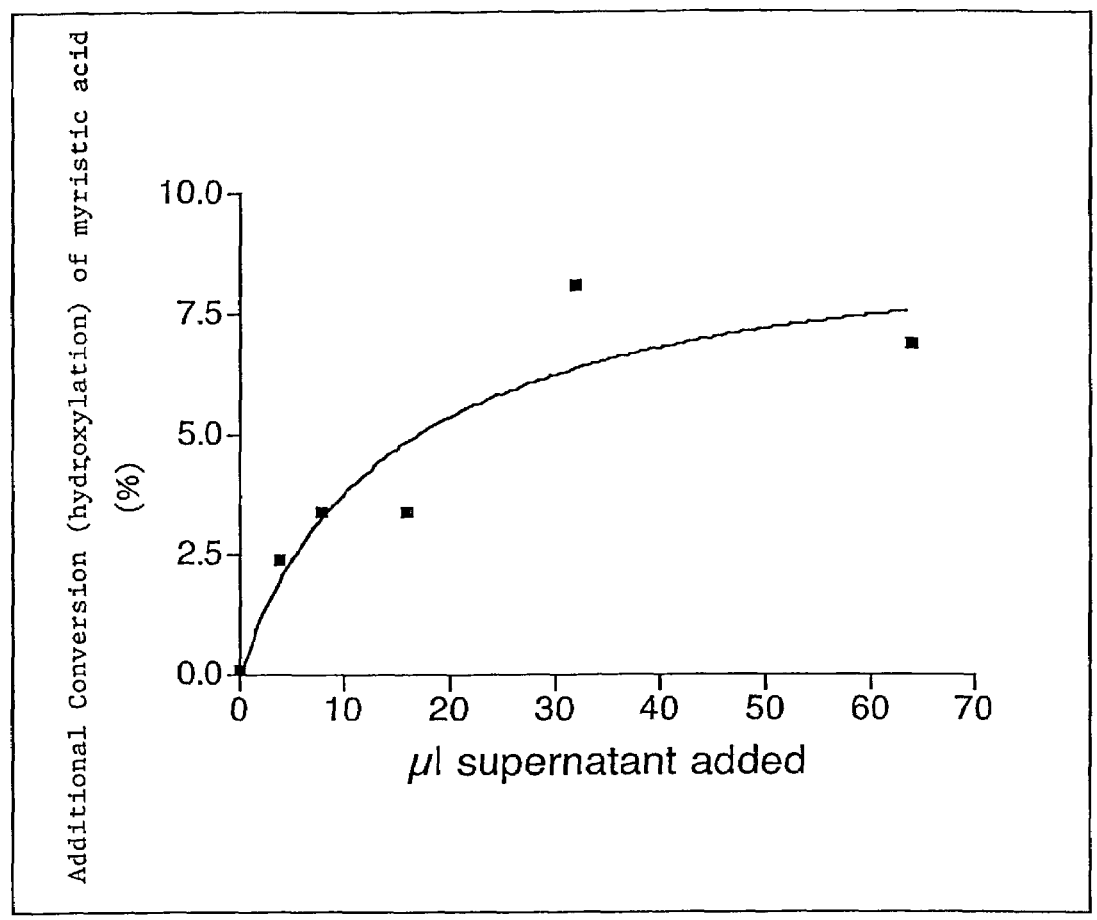
FIG. 9 graphically depicts enhancement of hydroxylation of myristic acid by CYP52A5A by addition of soluble CPR produced in Sf9 insect cells.

Soluble CPR produced in Sf9 cells was added to a standard reaction containing microsomes prepared from Sf9 cells expressing only CYP52A5A. The Enhancement of hydroxylation of [$^{14}$C]-myristic acid was fit to the hyperbola by a least-squares fit using the curve fitting algorithm of the program Prism (Prism Software, Inc.). Results are listed in Table 6. In addition, FIG. 9 shows the enhancement of hydroxylation of myristic acid by CYP52A5A by addition of soluble CPR produced in Sf9 insect cells. Iterative fit of the data to the simple Michaelis-Menton equation predicts a maximum enhancement of conversion of 9.3%, resulting in an approximately 2-fold higher conversion than the basal level of 10.1% conversion supported by the microsomes of Sf9 insect cells containing CYP52A5A and the Sf9 insect cells own cytochrome P450 reductase.

These results show that the soluble CPRA of the present invention is highly effective in activating cytochrome P450s.

Table 1

Primers used to clone CPRA and CYP52A5A into expression vectors.

CPRA codon change (internal primers to change CTG)
159U23 CTTGTCGACATTGAAGAAGAATA
150L23 TCAATGTCGACAAGACGTCTCTG
cloning (external primers introducing Xmal and Kpnl cloning sites)
991U32 CTACTCCCCGGGACCATGGCTTTAGA-CAAGTT
3029L32 GAGAAAGGTACCTCACTACCAMCATCT-TCTT
truncation (eliminate amino acids 1-31 of CPRA and introduce Ndel and BamHl sites)
cprsolU CTACTCCCCGGGCATATGGACACCGGGT-TCCT cprsolL GAGAAAGGATCCGGTACCTCACTAC-
CAAACATCTTCTT

CYP52A5A codon change (internal primers to change 1st CTG)
5ACTG1U ACCAAGTCGGTGCACAAGTTCAC
5ACTG1L TGCACCGACTTGGTACAGTCTCT
codon change (internal primers to change 2nd CTG)
5ACTG2U GTTAGATCTGACCCAGACGAGGT
5ACTG2L GGGTCAGATCTMCGTGGGAGAA
cloning (external primers introducing MamHl and Xbal cloning sites)
1U27 ACCACCGGATCCGCTATGATTGAACAA
1557L30 ACGCATTCTCTAGATCACTAGTCAAACTTG

TABLE 2

Plasmids Used for Expression

| Plasmid | Protein(s) expressed | Vector | Host cell |
|---|---|---|---|
| pFB15A | CYP52A5A | pFastBac1 | Sf9 Insect |
| pFB5ACPR | CYP52A5A + CPRA | pFastBacDual | Sf9 Insect |
| pFBsCPR | soluble CPRA | pFastBacDual | Sf9 Insect |
| pETsCPR | soluble CPRA | pET15b | E. coli |
| pTEVsCPR | soluble CPRA | PproEX-1 | E. coli |

TABLE 3

CPR specific activity (reduction of cytochrome c) in soluble and microsomal fractions of Sf9 cells containing different expression vectors.

| Host | Protein expressed | Fraction | Sp. Act. (µmol/min/mg) |
|---|---|---|---|
| Sf9 Insect | CYP52A5A | microsomes | 0.074 |
|  |  |  | 0.054 |
|  | CYP52A5A + CPRA | microsomes | 0.480 |
|  |  |  | 0.269 |
|  | Truncated (soluble) CPRA | soluble | 8.420 |
|  |  |  | 4.400 |

Each value represents a separate expression experiment in the Sf9 insect cells.

TABLE 4

Purification of soluble CPR from E. coli.

| Step | Total units µmoles cytochrome C reduced | Recovery (%) | Sp. Act. (µmol/min/mg) |
|---|---|---|---|
| Extract | 46000 | (100) | 5.3 |
| Ni-NTA column | 34000 | 75 | nd |
| Concentrated & dialyzed | 20000 | 44 | 420 | nd - not determined. Imidazol in buffer interferes with protein assay.

TABLE 5

ω-hydroxylation activity of cytochrome P450 with and without soluble CPR

| Proteins in microsomes | Soluble CPR[1] | net counts in product | ω-hydroxylauric acid (nmol) |
|---|---|---|---|
| CYP52A5A/CPRA | − | 12438 | 0.110 |
|  | + | 13218 | 0.115 |

TABLE 5-continued

ω-hydroxylation activity of cytochrome P450 with and without soluble CPR

| Proteins in microsomes | Soluble CPR[1] | net counts in product | ω-hydroxylauric acid (nmol) |
|---|---|---|---|
| CYP52A5A | − | 1798 | 0.015 |
|  | + | 7930 | 0.070 |

[1]provided in supernatant extracts of Sf9 insect cells expressing the truncated CPRA

TABLE 6

Enhancement of hydroxylation of $C^{14}$ myristic acid by addition of soluble CPR

| µl sCPR added | Conversion (%) | Enhancement (%) |
|---|---|---|
| 0 | 10 | 0 |
| 4 | 12.4 | 2.4 |
| 8 | 13.4 | 3.4 |
| 16 | 13.4 | 3.4 |
| 32 | 18.1 | 8.1 |
| 64 | 16.9 | 6.9 |

EXAMPLE 3

Figure 10:
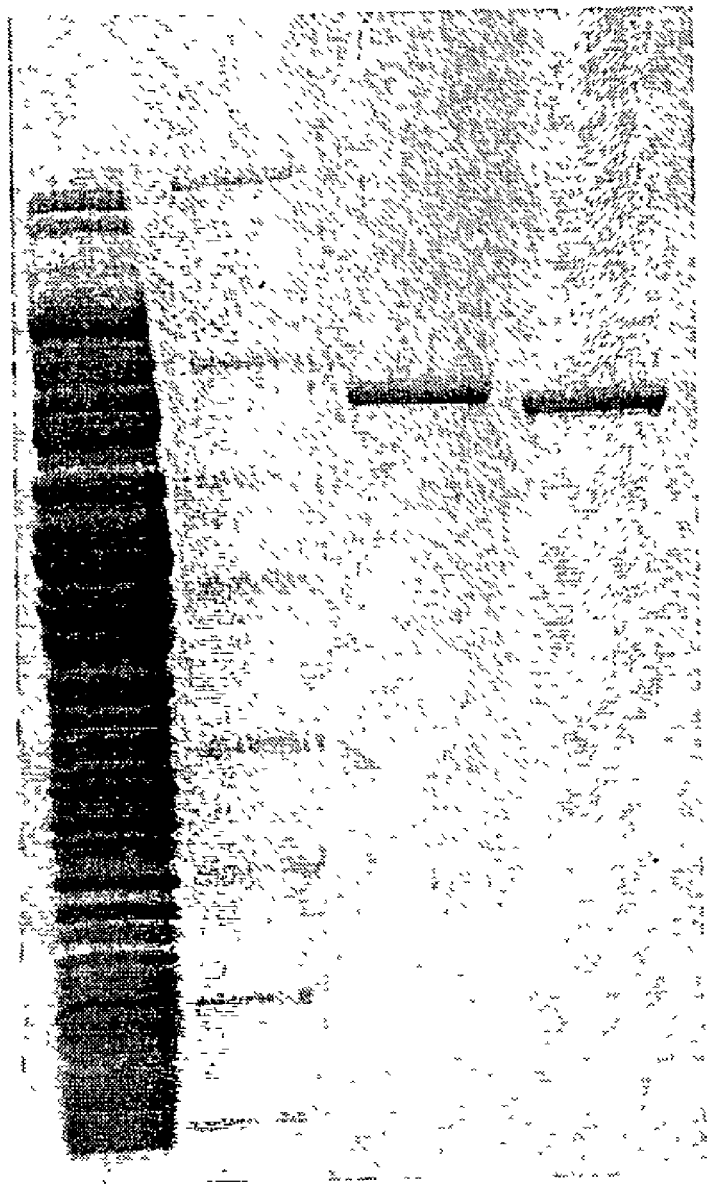
FIG. 10 is a protein gel (Commassie Blue stained) showing Purification of soluble CPR from *E. coli* and removal of his-tag leader sequence. Lane 1, crude *E. coli* extract; Lane 2, molecular weight markers; Lane 3, purified protein from Ni-NTA column before removal of leader; Lane 4, purified protein after treatment with TEV protease and purification on MonoQ. The resulting protein contains only two additional amino acids on its N-terminus. The specific activity of the protein in reduction of cytochrome c was 198 U/mg.

Production of a Soluble CPR in E. coli and Removal of the His-Taq Leader Sequence In order to produce a form of soluble CPR lacking the his-tag, the gene was transferred from the pETsCPR vector construct to the commercial vector pProEX-1 (Life Technologies). This vector appends an N-terminal sequence to the protein that includes a his-tag plus a TEV protease site for removal of the his-tag. The sCPR was expressed and purified as described in Example 2, then incubated overnight at 4° C. with commercial TEV protease (Life Technologies, Inc.) using the manufacturer's protocol. The digested material was then fractionated on a MonoQ column (Amersham-Pharmacia Biotech) to remove the protease, giving pure truncated sCPR lacking the his-tag (FIG. 10). The specific activity of this preparation was 198 U/mg. The loss of activity relative to the value of 420 U/mg is attributed to the increased processing time required for the removal of the his-tag and the instability of the soluble enzyme.

REFERENCES

Dignam, J. D. and Strobel, H. W. (1977) NADPH-cytochrome P-450 reductase from rat liver: purification by affinity chromatography and characterization. *Biochemistry*, 16, 1116–23.

GibcoBRL. Bac-to-Bac Baculovirus Expression Systems, Instruction Manual. Life Technologies.

Hara, A., Ueda, M., Misawa, S., Matsui, T., Furuhashi, K. and Tanaka, A. (2000) A mutated hygromycin resistance gene is functional in the n-alkane-assimilating yeast *Candida tropicalis*. *Arch Microbiol*, 173, 187–92.

Ho, S. N., Hunt, H. D., Horton, R. M., Pullen, J. K. and Pease, L. R. (1989) Site-directed mutagenesis by overlap extension using the polymerase chain reaction. *Gene*, 77, 51–9.

Hochuli, E., Bannwarth, W., Dobeli, H., Gentz, R. and Stuber, D. (1988) Genetic approach to facilitate purification of recombinant proteins with a novel metal chelate adsorbent. *Bio/Technology*, 6, 1321–1325.

Honeck, H., Schunck, W. H., Riege, P. and Muller, H. G. (1982) The cytochrome P-450 alkane monooxygenase system of the yeast Lodderomyces elongisporus: purification and some properties of the NADPH-cytochrome P-450 reductase. *Biochem Biophys Res Commun*, 106, 1318–24.

Hood, S. R., Girish, S. and Jones, P. (1997) Expression of cytochromes P450 in a Baculovirus system. In Philips, I. R. and Shepard, E. A. (eds.), *Methods in Molecular Biology*. Humana, Totowa, N.J., Vol. 107, pp. 203–218.

Lamb, D. C., Kelly, D. E., Venkateswarlu, K., Manning, N. J., Bligh, H. F., Schunck, W. H. and Kelly, S. L. (1999) Generation of a complete, soluble, and catalytically active sterol 14 alpha-demethylase-reductase complex. *Biochemistry*, 38, 8733–8.

Masters, B. S., Prough, R. A. and Kamin, H. (1975) Properties of the stable aerobic and anaerobic half-reduced states of NADPH-cytochrome c reductase. *Biochemistry*, 14, 607–13.

Skerra, A., Pfitzinger, I., and Pluckthun, A. (1991) The functional expression of antibody Fv fragment s in *Escherichia coli:*Improved vectors and a generally applicable purificatin technique, *Biotechnology* 9:273–278.

Scheller, U., Zimmer, T., Kargel, E. and Schunck, W. H. (1996) Characterization of the n-alkane and fatty acid hydroxylating cytochrome P450 forms 52A3 and 52A4. *Arch Biochem Biophys*, 328, 245–54.

Tsotsou, G. E., Cass, A. E. G., and Gilardi G. (2002) High throughput assay for cytochrome P450 BM3 for screening libraries of substrates and combinatorial mutants. *Biosensors and Bioelectronics* 17:119–131.

Ueda, T., Suzuki, T., Yokogawa, T., Nishikawa, K. and Watanabe, K. (1994) Unique structure of new serine tRNAs responsible for decoding leucine codon CUG in various *Candida* species and their putative ancestral tRNA genes. *Biochimie*, 76, 1217–22.

Venkateswarlu, K., Lamb, D. C., Kelly, D. E., Manning, N. J. and Kelly, S. L. (1998) The N-terminal membrane domain of yeast NADPH-cytochrome P450 (CYP) oxidoreductase is not required for catalytic activity in sterol biosynthesis or in reconstitution of CYP activity. *J Biol Chem*, 273, 4492–6.

Yabusaki, Y., Murakami, H., Sakaki, T., Shibata, M. and Ohkawa, H. (1988) Genetically engineered modification of P450 monooxygenases: functional analysis of the amino-terminal hydrophobic region and hinge region of the P450/reductase fused enzyme. *DNA*, 7, 701–11.

Yasukochi, Y. and Masters, B. S. (1976) Some properties of a detergent-solubilized NADPH-cytochrome c(cytochrome P-450) reductase purified by biospecific affinity chromatography. *J Biol Chem*, 251, 5337–44.n

---

What is claimed is:

1. An isolated host cell transformed with a nucleic acid molecule encoding a soluble cytochrome P450 reductase (CPR), the soluble CPR consisting of:
   the amino acid of SEQ ID NO:2; or
   the amino acid sequence of SEQ ID NO:2 further consisting of a translation initiation signal located before the first amino acid residue in SEQ ID NO:2.

2. The host cell of claim 1 which is a prokaryotic cell.

3. The host cell of claim 2 wherein the prokaryotic cell is *E. coli*.

4. The host cell of claim 1 which is a eukaryotic cell.

5. An isolated nucleic acid molecule encoding a soluble cytochrome P450 reductase (CPR) wherein said soluble CPR consists of the amino acid of SEQ ID NO:2.

6. The isolated nucleic acid molecule of claim 1 consisting of the nucleotide sequence of SEQ ID NO:1 or the nucleotide sequence consisting of SEQ ID NO:1 and a codon for a translational initiation signal at the 5'end of SEQ ID NO:1.

7. The isolated nucleic acid molecule of claim 6 wherein the translational signal is a sequence encoding a methionine residue.

8. A vector comprising the nucleic acid molecule of claim 5 or 7.

9. The vector of claim 8 wherein the vector is a plasmid, phagemid, phage or cosmid.

10. The vector of claim 8 wherein the vector is a linear vector.

11. An isolated host cell transfected or transformed with the nucleic acid molecule of claim 5 or 7.

12. An isolated host cell transformed or transfected with the vector of claim 8.

13. An isolated host cell transformed or transfected with the vector of claim 9.

14. An isolated host cell transformed or transfected with the vector of claim 10.

15. The host cell of claim 11 which is a prokaryotic cell.

16. The host cell of claim 12 which is a prokaryotic cell.

17. The host cell of claim 13 which is a prokaryotic cell.

18. The host cell of claim 14 wherein the prokaryotic cells are *E. coli* cells.

19. The host cell of claim 15 wherein the prokaryotic cells are *E. coli* cells.

20. The host cell of claim 16 wherein the prokaryotic cells are *E. coli* cells.

21. The host cell of claim 17 wherein the prokaryotic cells are *E. coli* cells.

22. The host cell of claim 11 which is a eukaryotic cell.

23. The host cell of claim 12 which is a eukaryotic cell.

24. The host cell of claim 13 which is a eukaryotic cell.

25. The host cell of claim 14 which is a eukaryotic cell.

26. The host cell according to claim 22 wherein the eukaryotic cell is a yeast cell from *Candida* sp.

27. The host cell according to claim 23 wherein the eukaryotic cell is a yeast cell from *Candida* sp.

28. The host cell according to claim 24 wherein the eukaryotic cell is a yeast cell from *Candida* sp.

29. The host cell according to claim 25 wherein the host cell is from *Candida tropicalis*.

30. A method for producing a soluble cytoebrome P450 reductase (CPR), said method comprising:
   (a) transforming a suitable host cell with a nucleotide sequence encoding a CPR consisting of SEQ ID NO: 2, wherein the nucleotide sequence is operably linked to a promoter which functions in the host cell and a codon for a translational start signal;
   (b) culturing the host cell for expression of the soluble CPR.

31. The method of claim 30 wherein the nucleotide sequence consists of SEQ ID NO: 1.

32. A method for producing a soluble cytochrome P450 reductase (CPR), said method comprising:
   a) transforming an isolated host cell with a nucleotide sequence encoding a CPR consisting of SEQ ID NO:2 and a heterologous peptide sequence located at the N-terminus of said CPR, wherein said nucleotide sequence is operably linked to a promoter which functions in said host cell and a translational initiation signal codon and wherein said heterologous peptide sequence is selected from the group consisting of a purification moiety, a secretion sequence and a signal peptide;
   b) culturing the host cell for expression of said soluble CPR having CPR activity; and
   c) isolating said soluble CPR.

33. The method of claim 32 wherein the purification moiety is a his-tag.

34. The method of claim 32 wherein the secretion sequence increases secretion of the CPR from the host cell.

35. The method of claim 32 or 34, wherein the secretion sequence is a OmpA secretion sequence or the signal peptide is an extracellular enzyme selected from the group consisting of a protease, amylase, cellulase, xylenase and lipase.

36. The method of claim 32, wherein the soluble CPR consists of the amino acid sequence of SEQ ID NO:2 or a CPR consisting of SEQ ID NO:2 and a translational initiation signal, a methionine residue, attached to the N-terminal end of SEQ ID NO:2.

37. The method of claim 30 wherein the coding sequence for the soluble CPR consists of the nucleotide sequence of SEQ ID NO:1.

38. The host cell of claim 1 wherein a heterologous peptide sequence comprising a purification moiety or secretion sequence is located at the N-terminal end of the CPR protein.

39. The host cell of claim 38 wherein the purification moiety is a his-tag.

* * * * *

SEQUENCE LISTING

<160> NUMBER OF SEQ ID NOS: 6

<210> SEQ ID NO 1
<211> LENGTH: 1944
<212> TYPE: DNA
<213> ORGANISM: Candida tropicalis
<220> FEATURE:
<221> NAME/KEY: CDS
<222> LOCATION: (1)..(1944)
<223> OTHER INFORMATION:

<400> SEQUENCE: 1

```
cag gac acc ggg ttc ctc aac acg gac agc gga agc aac tcc aga gac        48
Gln Asp Thr Gly Phe Leu Asn Thr Asp Ser Gly Ser Asn Ser Arg Asp
1               5                   10                  15 gtc ttg ctg aca ttg aag aag aat aat aaa aac acg ttg ttg ttg ttt        96
Val Leu Leu Thr Leu Lys Lys Asn Asn Lys Asn Thr Leu Leu Leu Phe
            20                  25                  30 ggg tcc cag acg ggt acg gca gaa gat tac gcc aac aaa ttg tcc aga       144
Gly Ser Gln Thr Gly Thr Ala Glu Asp Tyr Ala Asn Lys Leu Ser Arg
        35                  40                  45 gaa ttg cac tcc aga ttt ggc ttg aaa acg atg gtt gca gat ttc gct       192
Glu Leu His Ser Arg Phe Gly Leu Lys Thr Met Val Ala Asp Phe Ala
    50                  55                  60 gat tac gat tgg gat aac ttc gga gat atc acc gaa gac atc ttg gtg       240
Asp Tyr Asp Trp Asp Asn Phe Gly Asp Ile Thr Glu Asp Ile Leu Val
65                  70                  75                  80 ttt ttc att gtt gcc acc tat ggt gag ggt gaa cct acc gat aat gcc       288
Phe Phe Ile Val Ala Thr Tyr Gly Glu Gly Glu Pro Thr Asp Asn Ala
                85                  90                  95 gac gag ttc cac acc tgg ttg act gaa gaa gct gac act ttg agt acc       336
Asp Glu Phe His Thr Trp Leu Thr Glu Glu Ala Asp Thr Leu Ser Thr
            100                 105                 110
```

| | | |
|---|---|---|
| ttg aaa tac acc gtg ttc ggg ttg ggt aac tcc acg tac gag ttc ttc<br>Leu Lys Tyr Thr Val Phe Gly Leu Gly Asn Ser Thr Tyr Glu Phe Phe<br>115                        120                    125 | 384 |
| aat gcc att ggt aga aag ttt gac aga ttg ttg agc gag aaa ggt ggt<br>Asn Ala Ile Gly Arg Lys Phe Asp Arg Leu Leu Ser Glu Lys Gly Gly<br>    130                      135                    140 | 432 |
| gac agg ttt gct gaa tac gct gaa ggt gat gac ggt act ggc acc ttg<br>Asp Arg Phe Ala Glu Tyr Ala Glu Gly Asp Asp Gly Thr Gly Thr Leu<br>145                        150                    155                    160 | 480 |
| gac gaa gat ttc atg gcc tgg aag gac aat gtc ttt gac gcc ttg aag<br>Asp Glu Asp Phe Met Ala Trp Lys Asp Asn Val Phe Asp Ala Leu Lys<br>                  165                    170                    175 | 528 |
| aat gat ttg aac ttt gaa gaa aag gaa ttg aag tac gaa cca aac gtg<br>Asn Asp Leu Asn Phe Glu Glu Lys Glu Leu Lys Tyr Glu Pro Asn Val<br>            180                      185                    190 | 576 |
| aaa ttg act gag aga gac gac ttg tct gct gct gac tcc caa gtt tcc<br>Lys Leu Thr Glu Arg Asp Asp Leu Ser Ala Ala Asp Ser Gln Val Ser<br>                  195                    200                    205 | 624 |
| ttg ggt gag cca aac aag aag tac atc aac tcc gag ggc atc gac ttg<br>Leu Gly Glu Pro Asn Lys Lys Tyr Ile Asn Ser Glu Gly Ile Asp Leu<br>210                        215                    220 | 672 |
| acc aag ggt cca ttc gac cac acc cac cca tac ttg gcc aga atc acc<br>Thr Lys Gly Pro Phe Asp His Thr His Pro Tyr Leu Ala Arg Ile Thr<br>225                        230                    235                    240 | 720 |
| gag acg aga gag ttg ttc agc tcc aag gac aga cac tgt atc cac gtt<br>Glu Thr Arg Glu Leu Phe Ser Ser Lys Asp Arg His Cys Ile His Val<br>                  245                    250                    255 | 768 |
| gaa ttt gac att tct gaa tcg aac ttg aaa tac acc acc ggt gac cat<br>Glu Phe Asp Ile Ser Glu Ser Asn Leu Lys Tyr Thr Thr Gly Asp His<br>            260                      265                    270 | 816 |
| cta gct atc tgg cca tcc aac tcc gac gaa aac att aag caa ttt gcc<br>Leu Ala Ile Trp Pro Ser Asn Ser Asp Glu Asn Ile Lys Gln Phe Ala<br>                  275                    280                    285 | 864 |
| aag tgt ttc gga ttg gaa gat aaa ctc gac act gtt att gaa ttg aag<br>Lys Cys Phe Gly Leu Glu Asp Lys Leu Asp Thr Val Ile Glu Leu Lys<br>290                        295                    300 | 912 |
| gcg ttg gac tcc act tac acc atc cca ttc cca acc cca att acc tac<br>Ala Leu Asp Ser Thr Tyr Thr Ile Pro Phe Pro Thr Pro Ile Thr Tyr<br>305                        310                    315                    320 | 960 |
| ggt gct gtc att aga cac cat tta gaa atc tcc ggt cca gtc tcg aga<br>Gly Ala Val Ile Arg His His Leu Glu Ile Ser Gly Pro Val Ser Arg<br>                  325                    330                    335 | 1008 |
| caa ttc ttt ttg tca att gct ggg ttt gct cct gat gaa gaa aca aag<br>Gln Phe Phe Leu Ser Ile Ala Gly Phe Ala Pro Asp Glu Glu Thr Lys<br>            340                      345                    350 | 1056 |
| aag gct ttt acc aga ctt ggt ggt gac aag caa gaa ttc gcc gcc aag<br>Lys Ala Phe Thr Arg Leu Gly Gly Asp Lys Gln Glu Phe Ala Ala Lys<br>                  355                    360                    365 | 1104 |
| gtc acc cgc aga aag ttc aac att gcc gat gcc ttg tta tat tcc tcc<br>Val Thr Arg Arg Lys Phe Asn Ile Ala Asp Ala Leu Leu Tyr Ser Ser<br>370                        375                    380 | 1152 |
| aac aac gct cca tgg tcc gat gtt cct ttt gaa ttc ctt att gaa aac<br>Asn Asn Ala Pro Trp Ser Asp Val Pro Phe Glu Phe Leu Ile Glu Asn<br>385                        390                    395                    400 | 1200 |
| gtt cca cac ttg act cca cgt tac tac tcc att tcg tct tcg tca ttg<br>Val Pro His Leu Thr Pro Arg Tyr Tyr Ser Ile Ser Ser Ser Ser Leu<br>                  405                    410                    415 | 1248 |
| agt gaa aag caa ctc atc aac gtt act gca gtt gtt gaa gcc gaa gaa<br>Ser Glu Lys Gln Leu Ile Asn Val Thr Ala Val Val Glu Ala Glu Glu<br>            420                      425                    430 | 1296 |

```
gaa gct gat ggc aga cca gtc act ggt gtt gtc acc aac ttg ttg aag    1344
Glu Ala Asp Gly Arg Pro Val Thr Gly Val Val Thr Asn Leu Leu Lys
        435                 440                 445 aac gtt gaa att gtg caa aac aag act ggc gaa aag cca ctt gtc cac    1392
Asn Val Glu Ile Val Gln Asn Lys Thr Gly Glu Lys Pro Leu Val His
450                 455                 460 tac gat ttg agc ggc cca aga ggc aag ttc aac aag ttc aag ttg cca    1440
Tyr Asp Leu Ser Gly Pro Arg Gly Lys Phe Asn Lys Phe Lys Leu Pro
465                 470                 475                 480 gtg cat gtg aga aga tcc aac ttt aag ttg cca aag aac tcc acc acc    1488
Val His Val Arg Arg Ser Asn Phe Lys Leu Pro Lys Asn Ser Thr Thr
                485                 490                 495 cca gtt atc ttg att ggt cca ggt act ggt gtt gcc cca ttg aga ggt    1536
Pro Val Ile Leu Ile Gly Pro Gly Thr Gly Val Ala Pro Leu Arg Gly
            500                 505                 510 ttt gtc aga gaa aga gtt caa caa gtc aag aat ggt gtc aat gtt ggc    1584
Phe Val Arg Glu Arg Val Gln Gln Val Lys Asn Gly Val Asn Val Gly
        515                 520                 525 aag act ttg ttg ttt tat ggt tgc aga aac tcc aac gag gac ttt ttg    1632
Lys Thr Leu Leu Phe Tyr Gly Cys Arg Asn Ser Asn Glu Asp Phe Leu
530                 535                 540 tac aag caa gaa tgg gcc gag tac gct tct gtt ttg ggt gaa aac ttt    1680
Tyr Lys Gln Glu Trp Ala Glu Tyr Ala Ser Val Leu Gly Glu Asn Phe
545                 550                 555                 560 gag atg ttc aat gcc ttc tcc aga caa gac cca tcc aag aag gtt tac    1728
Glu Met Phe Asn Ala Phe Ser Arg Gln Asp Pro Ser Lys Lys Val Tyr
                565                 570                 575 gtc cag gat aag att tta gaa aac agc caa ctt gtg cac gag ttg ttg    1776
Val Gln Asp Lys Ile Leu Glu Asn Ser Gln Leu Val His Glu Leu Leu
            580                 585                 590 act gaa ggt gcc att atc tac gtc tgt ggt gat gcc agt aga atg gct    1824
Thr Glu Gly Ala Ile Ile Tyr Val Cys Gly Asp Ala Ser Arg Met Ala
        595                 600                 605 aga gac gtg cag acc aca att tcc aag att gtt gct aaa agc aga gaa    1872
Arg Asp Val Gln Thr Thr Ile Ser Lys Ile Val Ala Lys Ser Arg Glu
610                 615                 620 att agt gaa gac aag gct gct gaa ttg gtc aag tcc tgg aag gtc caa    1920
Ile Ser Glu Asp Lys Ala Ala Glu Leu Val Lys Ser Trp Lys Val Gln
625                 630                 635                 640 aat aga tac caa gaa gat gtt tgg                                    1944
Asn Arg Tyr Gln Glu Asp Val Trp
                645

<210> SEQ ID NO 2
<211> LENGTH: 648
<212> TYPE: PRT
<213> ORGANISM: Candida tropicalis

<400> SEQUENCE: 2

Gln Asp Thr Gly Phe Leu Asn Thr Asp Ser Gly Ser Asn Ser Arg Asp
1               5                   10                  15

Val Leu Leu Thr Leu Lys Lys Asn Asn Lys Asn Thr Leu Leu Leu Phe
            20                  25                  30

Gly Ser Gln Thr Gly Thr Ala Glu Asp Tyr Ala Asn Lys Leu Ser Arg
        35                  40                  45

Glu Leu His Ser Arg Phe Gly Leu Lys Thr Met Val Ala Asp Phe Ala
    50                  55                  60

Asp Tyr Asp Trp Asp Asn Phe Gly Asp Ile Thr Glu Asp Ile Leu Val
65                  70                  75                  80
```

-continued

```
Phe Phe Ile Val Ala Thr Tyr Gly Glu Gly Glu Pro Thr Asp Asn Ala
                85                  90                  95

Asp Glu Phe His Thr Trp Leu Thr Glu Glu Ala Asp Thr Leu Ser Thr
            100                 105                 110

Leu Lys Tyr Thr Val Phe Gly Leu Gly Asn Ser Thr Tyr Glu Phe Phe
            115                 120                 125

Asn Ala Ile Gly Arg Lys Phe Asp Arg Leu Leu Ser Glu Lys Gly Gly
        130                 135                 140

Asp Arg Phe Ala Glu Tyr Ala Glu Gly Asp Asp Gly Thr Gly Thr Leu
145                 150                 155                 160

Asp Glu Asp Phe Met Ala Trp Lys Asp Asn Val Phe Asp Ala Leu Lys
                165                 170                 175

Asn Asp Leu Asn Phe Glu Glu Lys Glu Leu Lys Tyr Glu Pro Asn Val
            180                 185                 190

Lys Leu Thr Glu Arg Asp Asp Leu Ser Ala Ala Asp Ser Gln Val Ser
        195                 200                 205

Leu Gly Glu Pro Asn Lys Lys Tyr Ile Asn Ser Glu Gly Ile Asp Leu
    210                 215                 220

Thr Lys Gly Pro Phe Asp His Thr His Pro Tyr Leu Ala Arg Ile Thr
225                 230                 235                 240

Glu Thr Arg Glu Leu Phe Ser Ser Lys Asp Arg His Cys Ile His Val
                245                 250                 255

Glu Phe Asp Ile Ser Glu Ser Asn Leu Lys Tyr Thr Thr Gly Asp His
            260                 265                 270

Leu Ala Ile Trp Pro Ser Asn Ser Asp Glu Asn Ile Lys Gln Phe Ala
        275                 280                 285

Lys Cys Phe Gly Leu Glu Asp Lys Leu Asp Thr Val Ile Glu Leu Lys
    290                 295                 300

Ala Leu Asp Ser Thr Tyr Thr Ile Pro Phe Pro Thr Pro Ile Thr Tyr
305                 310                 315                 320

Gly Ala Val Ile Arg His His Leu Glu Ile Ser Gly Pro Val Ser Arg
                325                 330                 335

Gln Phe Phe Leu Ser Ile Ala Gly Phe Ala Pro Asp Glu Glu Thr Lys
            340                 345                 350

Lys Ala Phe Thr Arg Leu Gly Gly Asp Lys Gln Glu Phe Ala Ala Lys
        355                 360                 365

Val Thr Arg Arg Lys Phe Asn Ile Ala Asp Ala Leu Leu Tyr Ser Ser
    370                 375                 380

Asn Asn Ala Pro Trp Ser Asp Val Pro Phe Glu Phe Leu Ile Glu Asn
385                 390                 395                 400

Val Pro His Leu Thr Pro Arg Tyr Tyr Ser Ile Ser Ser Ser Ser Leu
                405                 410                 415

Ser Glu Lys Gln Leu Ile Asn Val Thr Ala Val Val Glu Ala Glu Glu
            420                 425                 430

Glu Ala Asp Gly Arg Pro Val Thr Gly Val Val Thr Asn Leu Leu Lys
        435                 440                 445

Asn Val Glu Ile Val Gln Asn Lys Thr Gly Glu Lys Pro Leu Val His
    450                 455                 460

Tyr Asp Leu Ser Gly Pro Arg Gly Lys Phe Asn Lys Phe Lys Leu Pro
465                 470                 475                 480

Val His Val Arg Arg Ser Asn Phe Lys Leu Pro Lys Asn Ser Thr Thr
                485                 490                 495
```

```
Pro Val Ile Leu Ile Gly Pro Gly Thr Gly Val Ala Pro Leu Arg Gly
            500                 505                 510

Phe Val Arg Glu Arg Val Gln Gln Val Lys Asn Gly Val Asn Val Gly
            515                 520                 525

Lys Thr Leu Leu Phe Tyr Gly Cys Arg Asn Ser Asn Glu Asp Phe Leu
            530                 535                 540

Tyr Lys Gln Glu Trp Ala Glu Tyr Ala Ser Val Leu Gly Glu Asn Phe
545                 550                 555                 560

Glu Met Phe Asn Ala Phe Ser Arg Gln Asp Pro Ser Lys Lys Val Tyr
                565                 570                 575

Val Gln Asp Lys Ile Leu Glu Asn Ser Gln Leu Val His Glu Leu Leu
            580                 585                 590

Thr Glu Gly Ala Ile Ile Tyr Val Cys Gly Asp Ala Ser Arg Met Ala
            595                 600                 605

Arg Asp Val Gln Thr Thr Ile Ser Lys Ile Val Ala Lys Ser Arg Glu
            610                 615                 620

Ile Ser Glu Asp Lys Ala Ala Glu Leu Val Lys Ser Trp Lys Val Gln
625                 630                 635                 640

Asn Arg Tyr Gln Glu Asp Val Trp
                645

<210> SEQ ID NO 3
<211> LENGTH: 648
<212> TYPE: PRT
<213> ORGANISM: Candida tropicalis

<400> SEQUENCE: 3

Gln Asp Thr Gly Phe Leu Asn Thr Asp Ser Gly Ser Asn Ser Arg Asp
1               5                   10                  15

Val Leu Ser Thr Leu Lys Lys Asn Asn Lys Asn Thr Leu Leu Leu Phe
            20                  25                  30

Gly Ser Gln Thr Gly Thr Ala Glu Asp Tyr Ala Asn Lys Leu Ser Arg
            35                  40                  45

Glu Leu His Ser Arg Phe Gly Leu Lys Thr Met Val Ala Asp Phe Ala
        50                  55                  60

Asp Tyr Asp Trp Asp Asn Phe Gly Asp Ile Thr Glu Asp Ile Leu Val
65                  70                  75                  80

Phe Phe Ile Val Ala Thr Tyr Gly Glu Gly Glu Pro Thr Asp Asn Ala
                85                  90                  95

Asp Glu Phe His Thr Trp Leu Thr Glu Glu Ala Asp Thr Leu Ser Thr
            100                 105                 110

Leu Lys Tyr Thr Val Phe Gly Leu Gly Asn Ser Thr Tyr Glu Phe Phe
            115                 120                 125

Asn Ala Ile Gly Arg Lys Phe Asp Arg Leu Leu Ser Glu Lys Gly Gly
        130                 135                 140

Asp Arg Phe Ala Glu Tyr Ala Glu Gly Asp Asp Gly Thr Gly Thr Leu
145                 150                 155                 160

Asp Glu Asp Phe Met Ala Trp Lys Asp Asn Val Phe Asp Ala Leu Lys
                165                 170                 175

Asn Asp Leu Asn Phe Glu Glu Lys Glu Leu Lys Tyr Glu Pro Asn Val
            180                 185                 190

Lys Leu Thr Glu Arg Asp Asp Leu Ser Ala Ala Asp Ser Gln Val Ser
            195                 200                 205

Leu Gly Glu Pro Asn Lys Lys Tyr Ile Asn Ser Glu Gly Ile Asp Leu
        210                 215                 220
```

-continued

```
Thr Lys Gly Pro Phe Asp His Thr His Pro Tyr Leu Ala Arg Ile Thr
225                 230                 235                 240

Glu Thr Arg Glu Leu Phe Ser Ser Lys Asp Arg His Cys Ile His Val
            245                 250                 255

Glu Phe Asp Ile Ser Glu Ser Asn Leu Lys Tyr Thr Thr Gly Asp His
            260                 265                 270

Leu Ala Ile Trp Pro Ser Asn Ser Asp Glu Asn Ile Lys Gln Phe Ala
            275                 280                 285

Lys Cys Phe Gly Leu Glu Asp Lys Leu Asp Thr Val Ile Glu Leu Lys
290                 295                 300

Ala Leu Asp Ser Thr Tyr Thr Ile Pro Phe Pro Thr Pro Ile Thr Tyr
305                 310                 315                 320

Gly Ala Val Ile Arg His His Leu Glu Ile Ser Gly Pro Val Ser Arg
                325                 330                 335

Gln Phe Phe Leu Ser Ile Ala Gly Phe Ala Pro Asp Glu Glu Thr Lys
                340                 345                 350

Lys Ala Phe Thr Arg Leu Gly Gly Asp Lys Gln Glu Phe Ala Ala Lys
                355                 360                 365

Val Thr Arg Arg Lys Phe Asn Ile Ala Asp Ala Leu Leu Tyr Ser Ser
370                 375                 380

Asn Asn Ala Pro Trp Ser Asp Val Pro Phe Glu Phe Leu Ile Glu Asn
385                 390                 395                 400

Val Pro His Leu Thr Pro Arg Tyr Tyr Ser Ile Ser Ser Ser Ser Leu
                405                 410                 415

Ser Glu Lys Gln Leu Ile Asn Val Thr Ala Val Val Glu Ala Glu Glu
                420                 425                 430

Glu Ala Asp Gly Arg Pro Val Thr Gly Val Val Thr Asn Leu Leu Lys
                435                 440                 445

Asn Val Glu Ile Val Gln Asn Lys Thr Gly Glu Lys Pro Leu Val His
                450                 455                 460

Tyr Asp Leu Ser Gly Pro Arg Gly Lys Phe Asn Lys Phe Lys Leu Pro
465                 470                 475                 480

Val His Val Arg Arg Ser Asn Phe Lys Leu Pro Lys Asn Ser Thr Thr
                485                 490                 495

Pro Val Ile Leu Ile Gly Pro Gly Thr Gly Val Ala Pro Leu Arg Gly
                500                 505                 510

Phe Val Arg Glu Arg Val Gln Gln Val Lys Asn Gly Val Asn Val Gly
                515                 520                 525

Lys Thr Leu Leu Phe Tyr Gly Cys Arg Asn Ser Asn Glu Asp Phe Leu
530                 535                 540

Tyr Lys Gln Glu Trp Ala Glu Tyr Ala Ser Val Leu Gly Glu Asn Phe
545                 550                 555                 560

Glu Met Phe Asn Ala Phe Ser Arg Gln Asp Pro Ser Lys Lys Val Tyr
                565                 570                 575

Val Gln Asp Lys Ile Leu Glu Asn Ser Gln Leu Val His Glu Leu Leu
                580                 585                 590

Thr Glu Gly Ala Ile Ile Tyr Val Cys Gly Asp Ala Ser Arg Met Ala
                595                 600                 605

Arg Asp Val Gln Thr Thr Ile Ser Lys Ile Val Ala Lys Ser Arg Glu
        610                 615                 620

Ile Ser Glu Asp Lys Ala Ala Glu Leu Val Lys Ser Trp Lys Val Gln
625                 630                 635                 640
```

Asn Arg Tyr Gln Glu Asp Val Trp
                 645

<210> SEQ ID NO 4
<211> LENGTH: 1944
<212> TYPE: DNA
<213> ORGANISM: Candida tropicalis
<220> FEATURE:
<221> NAME/KEY: CDS
<222> LOCATION: (1)..(1944)
<223> OTHER INFORMATION:

<400> SEQUENCE: 4

| | | | | | | | | | | | | | | | | |
|---|---|---|---|---|---|---|---|---|---|---|---|---|---|---|---|---|
| cag | gac | acc | ggg | ttc | ctc | aac | acg | gac | agc | gga | agc | aac | tcc | aga | gac | 48 |
| Gln | Asp | Thr | Gly | Phe | Leu | Asn | Thr | Asp | Ser | Gly | Ser | Asn | Ser | Arg | Asp | |
| 1 | | | | 5 | | | | | 10 | | | | | 15 | | |

| gtc | ttg | ctg | aca | ttg | aag | aag | aat | aat | aaa | aac | acg | ttg | ttg | ttg | ttt | 96 |
|---|---|---|---|---|---|---|---|---|---|---|---|---|---|---|---|---|
| Val | Leu | Leu | Thr | Leu | Lys | Lys | Asn | Asn | Lys | Asn | Thr | Leu | Leu | Leu | Phe | |
| | | | 20 | | | | | 25 | | | | | 30 | | | |

| ggg | tcc | cag | acc | ggt | acg | gca | gaa | gat | tac | gcc | aac | aaa | ttg | tca | aga | 144 |
|---|---|---|---|---|---|---|---|---|---|---|---|---|---|---|---|---|
| Gly | Ser | Gln | Thr | Gly | Thr | Ala | Glu | Asp | Tyr | Ala | Asn | Lys | Leu | Ser | Arg | |
| | | 35 | | | | | 40 | | | | | 45 | | | | |

| gaa | ttg | cac | tcc | aga | ttt | ggc | ttg | aaa | acc | atg | gtt | gca | gat | ttc | gct | 192 |
|---|---|---|---|---|---|---|---|---|---|---|---|---|---|---|---|---|
| Glu | Leu | His | Ser | Arg | Phe | Gly | Leu | Lys | Thr | Met | Val | Ala | Asp | Phe | Ala | |
| 50 | | | | | 55 | | | | | 60 | | | | | | |

| gat | tac | gat | tgg | gat | aac | ttc | gga | gat | atc | acc | gaa | gat | atc | ttg | gtg | 240 |
|---|---|---|---|---|---|---|---|---|---|---|---|---|---|---|---|---|
| Asp | Tyr | Asp | Trp | Asp | Asn | Phe | Gly | Asp | Ile | Thr | Glu | Asp | Ile | Leu | Val | |
| 65 | | | | 70 | | | | | 75 | | | | | 80 | | |

| ttt | ttc | atc | gtt | gcc | acc | tac | ggt | gag | ggt | gaa | cct | acc | gac | aat | gcc | 288 |
|---|---|---|---|---|---|---|---|---|---|---|---|---|---|---|---|---|
| Phe | Phe | Ile | Val | Ala | Thr | Tyr | Gly | Glu | Gly | Glu | Pro | Thr | Asp | Asn | Ala | |
| | | | | 85 | | | | | 90 | | | | | 95 | | |

| gac | gag | ttc | cac | acc | tgg | ttg | act | gaa | gaa | gct | gac | act | ttg | agt | act | 336 |
|---|---|---|---|---|---|---|---|---|---|---|---|---|---|---|---|---|
| Asp | Glu | Phe | His | Thr | Trp | Leu | Thr | Glu | Glu | Ala | Asp | Thr | Leu | Ser | Thr | |
| | | | 100 | | | | | 105 | | | | | 110 | | | |

| ttg | aga | tat | acc | gtg | ttc | ggg | ttg | ggt | aac | tcc | acc | tac | gag | ttc | ttc | 384 |
|---|---|---|---|---|---|---|---|---|---|---|---|---|---|---|---|---|
| Leu | Arg | Tyr | Thr | Val | Phe | Gly | Leu | Gly | Asn | Ser | Thr | Tyr | Glu | Phe | Phe | |
| | | 115 | | | | | 120 | | | | | 125 | | | | |

| aat | gct | att | ggt | aga | aag | ttt | gac | aga | ttg | ttg | agt | gag | aaa | ggt | ggt | 432 |
|---|---|---|---|---|---|---|---|---|---|---|---|---|---|---|---|---|
| Asn | Ala | Ile | Gly | Arg | Lys | Phe | Asp | Arg | Leu | Leu | Ser | Glu | Lys | Gly | Gly | |
| | 130 | | | | | 135 | | | | | 140 | | | | | |

| gac | aga | ttt | gct | gaa | tat | gct | gaa | ggt | gac | gac | ggc | act | ggc | acc | ttg | 480 |
|---|---|---|---|---|---|---|---|---|---|---|---|---|---|---|---|---|
| Asp | Arg | Phe | Ala | Glu | Tyr | Ala | Glu | Gly | Asp | Asp | Gly | Thr | Gly | Thr | Leu | |
| 145 | | | | | 150 | | | | | 155 | | | | | 160 | |

| gac | gaa | gat | ttc | atg | gcc | tgg | aag | gat | aat | gtc | ttt | gac | gcc | ttg | aag | 528 |
|---|---|---|---|---|---|---|---|---|---|---|---|---|---|---|---|---|
| Asp | Glu | Asp | Phe | Met | Ala | Trp | Lys | Asp | Asn | Val | Phe | Asp | Ala | Leu | Lys | |
| | | | | 165 | | | | | 170 | | | | | 175 | | |

| aat | gac | ttg | aac | ttt | gaa | gaa | aag | gaa | ttg | aag | tac | gaa | cca | aac | gtg | 576 |
|---|---|---|---|---|---|---|---|---|---|---|---|---|---|---|---|---|
| Asn | Asp | Leu | Asn | Phe | Glu | Glu | Lys | Glu | Leu | Lys | Tyr | Glu | Pro | Asn | Val | |
| | | | 180 | | | | | 185 | | | | | 190 | | | |

| aaa | ttg | act | gag | aga | gat | gac | ttg | tct | gct | gcc | gac | tcc | caa | gtt | tcc | 624 |
|---|---|---|---|---|---|---|---|---|---|---|---|---|---|---|---|---|
| Lys | Leu | Thr | Glu | Arg | Asp | Asp | Leu | Ser | Ala | Ala | Asp | Ser | Gln | Val | Ser | |
| | | 195 | | | | | 200 | | | | | 205 | | | | |

| ttg | ggt | gag | cca | aac | aag | aag | tac | atc | aac | tcc | gag | ggc | atc | gac | ttg | 672 |
|---|---|---|---|---|---|---|---|---|---|---|---|---|---|---|---|---|
| Leu | Gly | Glu | Pro | Asn | Lys | Lys | Tyr | Ile | Asn | Ser | Glu | Gly | Ile | Asp | Leu | |
| | 210 | | | | | 215 | | | | | 220 | | | | | |

| acc | aag | ggt | cca | ttc | gac | cac | acc | cac | cca | tac | ttg | gcc | agg | atc | acc | 720 |
|---|---|---|---|---|---|---|---|---|---|---|---|---|---|---|---|---|
| Thr | Lys | Gly | Pro | Phe | Asp | His | Thr | His | Pro | Tyr | Leu | Ala | Arg | Ile | Thr | |
| 225 | | | | | 230 | | | | | 235 | | | | | 240 | |

| gag | acc | aga | gag | ttg | ttc | agc | tcc | aag | gaa | aga | cac | tgt | att | cac | gtt | 768 |
|---|---|---|---|---|---|---|---|---|---|---|---|---|---|---|---|---|
| Glu | Thr | Arg | Glu | Leu | Phe | Ser | Ser | Lys | Glu | Arg | His | Cys | Ile | His | Val | |
| | | | | 245 | | | | | 250 | | | | | 255 | | |

-continued

| | | |
|---|---|---|
| gaa ttt gac att tct gaa tcg aac ttg aaa tac acc acc ggt gac cat<br>Glu Phe Asp Ile Ser Glu Ser Asn Leu Lys Tyr Thr Thr Gly Asp His<br>          260                    265                    270 | | 816 |
| cta gcc atc tgg cca tcc aac tcc gac gaa aac atc aag caa ttt gcc<br>Leu Ala Ile Trp Pro Ser Asn Ser Asp Glu Asn Ile Lys Gln Phe Ala<br>              275                    280                    285 | | 864 |
| aag tgt ttc gga ttg gaa gat aaa ctc gac act gtt att gaa ttg aag<br>Lys Cys Phe Gly Leu Glu Asp Lys Leu Asp Thr Val Ile Glu Leu Lys<br>290                    295                    300 | | 912 |
| gca ttg gac tcc act tac acc att cca ttc cca act cca att act tac<br>Ala Leu Asp Ser Thr Tyr Thr Ile Pro Phe Pro Thr Pro Ile Thr Tyr<br>305                    310                    315                    320 | | 960 |
| ggt gct gtc att aga cac cat tta gaa atc tcc ggt cca gtc tcg aga<br>Gly Ala Val Ile Arg His His Leu Glu Ile Ser Gly Pro Val Ser Arg<br>                  325                    330                    335 | | 1008 |
| caa ttc ttt ttg tcg att gct ggg ttt gct cct gat gaa gaa aca aag<br>Gln Phe Phe Leu Ser Ile Ala Gly Phe Ala Pro Asp Glu Glu Thr Lys<br>              340                    345                    350 | | 1056 |
| aag act ttc acc aga ctt ggt ggt gac aaa caa gaa ttc gcc acc aag<br>Lys Thr Phe Thr Arg Leu Gly Gly Asp Lys Gln Glu Phe Ala Thr Lys<br>            355                    360                    365 | | 1104 |
| gtt acc cgc aga aag ttc aac att gcc gat gcc ttg tta tat tcc tcc<br>Val Thr Arg Arg Lys Phe Asn Ile Ala Asp Ala Leu Leu Tyr Ser Ser<br>370                    375                    380 | | 1152 |
| aac aac act cca tgg tcc gat gtt cct ttt gag ttc ctt att gaa aac<br>Asn Asn Thr Pro Trp Ser Asp Val Pro Phe Glu Phe Leu Ile Glu Asn<br>385                    390                    395                    400 | | 1200 |
| atc caa cac ttg act cca cgt tac tac tcc att tct tct tcg tcg ttg<br>Ile Gln His Leu Thr Pro Arg Tyr Tyr Ser Ile Ser Ser Ser Ser Leu<br>                  405                    410                    415 | | 1248 |
| agt gaa aaa caa ctc atc aat gtt act gca gtc gtt gag gcc gaa gaa<br>Ser Glu Lys Gln Leu Ile Asn Val Thr Ala Val Val Glu Ala Glu Glu<br>            420                    425                    430 | | 1296 |
| gaa gcc gat ggc aga cca gtc act ggt gtt gtt acc aac ttg ttg aag<br>Glu Ala Asp Gly Arg Pro Val Thr Gly Val Val Thr Asn Leu Leu Lys<br>                435                    440                    445 | | 1344 |
| aac att gaa att gcg caa aac aag act ggc gaa aag cca ctt gtt cac<br>Asn Ile Glu Ile Ala Gln Asn Lys Thr Gly Glu Lys Pro Leu Val His<br>450                    455                    460 | | 1392 |
| tac gat ttg agc ggc cca aga ggc aag ttc aac aag ttc aag ttg cca<br>Tyr Asp Leu Ser Gly Pro Arg Gly Lys Phe Asn Lys Phe Lys Leu Pro<br>465                    470                    475                    480 | | 1440 |
| gtg cac gtg aga aga tcc aac ttt aag ttg cca aag aac tcc acc acc<br>Val His Val Arg Arg Ser Asn Phe Lys Leu Pro Lys Asn Ser Thr Thr<br>                485                    490                    495 | | 1488 |
| cca gtt atc ttg att ggt cca ggt act ggt gtt gcc cca ttg aga ggt<br>Pro Val Ile Leu Ile Gly Pro Gly Thr Gly Val Ala Pro Leu Arg Gly<br>            500                    505                    510 | | 1536 |
| ttc gtt aga gaa aga gtt caa caa gtc aag aat ggt gtc aat gtt ggc<br>Phe Val Arg Glu Arg Val Gln Gln Val Lys Asn Gly Val Asn Val Gly<br>            515                    520                    525 | | 1584 |
| aag act ttg ttg ttt tat ggt tgc aga aac tcc aac gag gac ttt ttg<br>Lys Thr Leu Leu Phe Tyr Gly Cys Arg Asn Ser Asn Glu Asp Phe Leu<br>530                    535                    540 | | 1632 |
| tac aag caa gaa tgg gcc gag tac gct tct gtt ttg ggt gaa aac ttt<br>Tyr Lys Gln Glu Trp Ala Glu Tyr Ala Ser Val Leu Gly Glu Asn Phe<br>545                    550                    555                    560 | | 1680 |
| gag atg ttc aat gcc ttc tct aga caa gac cca tcc aag aag gtt tac<br>Glu Met Phe Asn Ala Phe Ser Arg Gln Asp Pro Ser Lys Lys Val Tyr<br>                565                    570                    575 | | 1728 |

```
gtc cag gat aag att tta gaa aac agc caa ctt gtg cac gaa ttg ttg      1776
Val Gln Asp Lys Ile Leu Glu Asn Ser Gln Leu Val His Glu Leu Leu
            580                 585                 590 acc gaa ggt gcc att atc tac gtc tgt ggt gac gcc agt aga atg gcc      1824
Thr Glu Gly Ala Ile Ile Tyr Val Cys Gly Asp Ala Ser Arg Met Ala
        595                 600                 605 aga gac gtc cag acc acg atc tcc aag att gtt gcc aaa agc aga gaa      1872
Arg Asp Val Gln Thr Thr Ile Ser Lys Ile Val Ala Lys Ser Arg Glu
    610                 615                 620 atc agt gaa gac aag gcc gct gaa ttg gtc aag tcc tgg aaa gtc caa      1920
Ile Ser Glu Asp Lys Ala Ala Glu Leu Val Lys Ser Trp Lys Val Gln
625                 630                 635                 640 aat aga tac caa gaa gat gtt tgg                                      1944
Asn Arg Tyr Gln Glu Asp Val Trp
                645

<210> SEQ ID NO 5
<211> LENGTH: 648
<212> TYPE: PRT
<213> ORGANISM: Candida tropicalis

<400> SEQUENCE: 5

Gln Asp Thr Gly Phe Leu Asn Thr Asp Ser Gly Ser Asn Ser Arg Asp
1               5                   10                  15

Val Leu Leu Thr Leu Lys Lys Asn Asn Lys Asn Thr Leu Leu Leu Phe
            20                  25                  30

Gly Ser Gln Thr Gly Thr Ala Glu Asp Tyr Ala Asn Lys Leu Ser Arg
        35                  40                  45

Glu Leu His Ser Arg Phe Gly Leu Lys Thr Met Val Ala Asp Phe Ala
    50                  55                  60

Asp Tyr Asp Trp Asp Asn Phe Gly Asp Ile Thr Glu Asp Ile Leu Val
65                  70                  75                  80

Phe Phe Ile Val Ala Thr Tyr Gly Glu Gly Glu Pro Thr Asp Asn Ala
                85                  90                  95

Asp Glu Phe His Thr Trp Leu Thr Glu Glu Ala Asp Thr Leu Ser Thr
            100                 105                 110

Leu Arg Tyr Thr Val Phe Gly Leu Gly Asn Ser Thr Tyr Glu Phe Phe
        115                 120                 125

Asn Ala Ile Gly Arg Lys Phe Asp Arg Leu Leu Ser Glu Lys Gly Gly
    130                 135                 140

Asp Arg Phe Ala Glu Tyr Ala Glu Gly Asp Asp Gly Thr Gly Thr Leu
145                 150                 155                 160

Asp Glu Asp Phe Met Ala Trp Lys Asp Asn Val Phe Asp Ala Leu Lys
                165                 170                 175

Asn Asp Leu Asn Phe Glu Glu Lys Glu Leu Lys Tyr Glu Pro Asn Val
            180                 185                 190

Lys Leu Thr Glu Arg Asp Asp Leu Ser Ala Ala Asp Ser Gln Val Ser
        195                 200                 205

Leu Gly Glu Pro Asn Lys Lys Tyr Ile Asn Ser Glu Gly Ile Asp Leu
    210                 215                 220

Thr Lys Gly Pro Phe Asp His Thr His Pro Tyr Leu Ala Arg Ile Thr
225                 230                 235                 240

Glu Thr Arg Glu Leu Phe Ser Ser Lys Glu Arg His Cys Ile His Val
                245                 250                 255

Glu Phe Asp Ile Ser Glu Ser Asn Leu Lys Tyr Thr Thr Gly Asp His
            260                 265                 270
```

```
Leu Ala Ile Trp Pro Ser Asn Ser Asp Glu Asn Ile Lys Gln Phe Ala
            275                 280                 285

Lys Cys Phe Gly Leu Glu Asp Lys Leu Asp Thr Val Ile Glu Leu Lys
        290                 295                 300

Ala Leu Asp Ser Thr Tyr Thr Ile Pro Phe Pro Thr Pro Ile Thr Tyr
305                 310                 315                 320

Gly Ala Val Ile Arg His His Leu Glu Ile Ser Gly Pro Val Ser Arg
                325                 330                 335

Gln Phe Phe Leu Ser Ile Ala Gly Phe Ala Pro Asp Glu Glu Thr Lys
            340                 345                 350

Lys Thr Phe Thr Arg Leu Gly Gly Asp Lys Gln Glu Phe Ala Thr Lys
        355                 360                 365

Val Thr Arg Arg Lys Phe Asn Ile Ala Asp Ala Leu Leu Tyr Ser Ser
    370                 375                 380

Asn Asn Thr Pro Trp Ser Asp Val Pro Phe Glu Phe Leu Ile Glu Asn
385                 390                 395                 400

Ile Gln His Leu Thr Pro Arg Tyr Tyr Ser Ile Ser Ser Ser Ser Leu
                405                 410                 415

Ser Glu Lys Gln Leu Ile Asn Val Thr Ala Val Val Glu Ala Glu Glu
            420                 425                 430

Glu Ala Asp Gly Arg Pro Val Thr Gly Val Val Thr Asn Leu Leu Lys
        435                 440                 445

Asn Ile Glu Ile Ala Gln Asn Lys Thr Gly Glu Lys Pro Leu Val His
    450                 455                 460

Tyr Asp Leu Ser Gly Pro Arg Gly Lys Phe Asn Lys Phe Lys Leu Pro
465                 470                 475                 480

Val His Val Arg Arg Ser Asn Phe Lys Leu Pro Lys Asn Ser Thr Thr
                485                 490                 495

Pro Val Ile Leu Ile Gly Pro Gly Thr Gly Val Ala Pro Leu Arg Gly
            500                 505                 510

Phe Val Arg Glu Arg Val Gln Gln Val Lys Asn Gly Val Asn Val Gly
        515                 520                 525

Lys Thr Leu Leu Phe Tyr Gly Cys Arg Asn Ser Asn Glu Asp Phe Leu
    530                 535                 540

Tyr Lys Gln Glu Trp Ala Glu Tyr Ala Ser Val Leu Gly Glu Asn Phe
545                 550                 555                 560

Glu Met Phe Asn Ala Phe Ser Arg Gln Asp Pro Ser Lys Lys Val Tyr
                565                 570                 575

Val Gln Asp Lys Ile Leu Glu Asn Ser Gln Leu Val His Glu Leu Leu
            580                 585                 590

Thr Glu Gly Ala Ile Ile Tyr Val Cys Gly Asp Ala Ser Arg Met Ala
        595                 600                 605

Arg Asp Val Gln Thr Thr Ile Ser Lys Ile Val Ala Lys Ser Arg Glu
    610                 615                 620

Ile Ser Glu Asp Lys Ala Ala Glu Leu Val Lys Ser Trp Lys Val Gln
625                 630                 635                 640

Asn Arg Tyr Gln Glu Asp Val Trp
                645

<210> SEQ ID NO 6
<211> LENGTH: 648
<212> TYPE: PRT
<213> ORGANISM: Candida tropicalis
```

<400> SEQUENCE: 6

```
Gln Asp Thr Gly Phe Leu Asn Thr Asp Ser Gly Ser Asn Ser Arg Asp
 1               5                  10                  15

Val Leu Ser Thr Leu Lys Lys Asn Asn Lys Asn Thr Leu Leu Leu Phe
            20                  25                  30

Gly Ser Gln Thr Gly Thr Ala Glu Asp Tyr Ala Asn Lys Leu Ser Arg
        35                  40                  45

Glu Leu His Ser Arg Phe Gly Leu Lys Thr Met Val Ala Asp Phe Ala
    50                  55                  60

Asp Tyr Asp Trp Asp Asn Phe Gly Asp Ile Thr Glu Asp Ile Leu Val
65                  70                  75                  80

Phe Phe Ile Val Ala Thr Tyr Gly Glu Gly Glu Pro Thr Asp Asn Ala
                85                  90                  95

Asp Glu Phe His Thr Trp Leu Thr Glu Glu Ala Asp Thr Leu Ser Thr
            100                 105                 110

Leu Arg Tyr Thr Val Phe Gly Leu Gly Asn Ser Thr Tyr Glu Phe Phe
        115                 120                 125

Asn Ala Ile Gly Arg Lys Phe Asp Arg Leu Leu Ser Glu Lys Gly Gly
130                 135                 140

Asp Arg Phe Ala Glu Tyr Ala Glu Gly Asp Asp Gly Thr Gly Thr Leu
145                 150                 155                 160

Asp Glu Asp Phe Met Ala Trp Lys Asp Asn Val Phe Asp Ala Leu Lys
                165                 170                 175

Asn Asp Leu Asn Phe Glu Glu Lys Glu Leu Lys Tyr Glu Pro Asn Val
            180                 185                 190

Lys Leu Thr Glu Arg Asp Asp Leu Ser Ala Ala Asp Ser Gln Val Ser
        195                 200                 205

Leu Gly Glu Pro Asn Lys Lys Tyr Ile Asn Ser Glu Gly Ile Asp Leu
    210                 215                 220

Thr Lys Gly Pro Phe Asp His Thr His Pro Tyr Leu Ala Arg Ile Thr
225                 230                 235                 240

Glu Thr Arg Glu Leu Phe Ser Ser Lys Glu Arg His Cys Ile His Val
                245                 250                 255

Glu Phe Asp Ile Ser Glu Ser Asn Leu Lys Tyr Thr Thr Gly Asp His
            260                 265                 270

Leu Ala Ile Trp Pro Ser Asn Ser Asp Glu Asn Ile Lys Gln Phe Ala
        275                 280                 285

Lys Cys Phe Gly Leu Glu Asp Lys Leu Asp Thr Val Ile Glu Leu Lys
290                 295                 300

Ala Leu Asp Ser Thr Tyr Thr Ile Pro Phe Pro Thr Pro Ile Thr Tyr
305                 310                 315                 320

Gly Ala Val Ile Arg His His Leu Glu Ile Ser Gly Pro Val Ser Arg
                325                 330                 335

Gln Phe Phe Leu Ser Ile Ala Gly Phe Ala Pro Asp Glu Glu Thr Lys
            340                 345                 350

Lys Thr Phe Thr Arg Leu Gly Gly Asp Lys Gln Glu Phe Ala Thr Lys
        355                 360                 365

Val Thr Arg Arg Lys Phe Asn Ile Ala Asp Ala Leu Leu Tyr Ser Ser
    370                 375                 380

Asn Asn Thr Pro Trp Ser Asp Val Pro Phe Glu Phe Leu Ile Glu Asn
385                 390                 395                 400

Ile Gln His Leu Thr Pro Arg Tyr Tyr Ser Ile Ser Ser Ser Ser Leu
                405                 410                 415
```

-continued

```
Ser Glu Lys Gln Leu Ile Asn Val Thr Ala Val Val Glu Ala Glu Glu
            420                 425                 430

Glu Ala Asp Gly Arg Pro Val Thr Gly Val Val Thr Asn Leu Leu Lys
        435                 440                 445

Asn Ile Glu Ile Ala Gln Asn Lys Thr Gly Glu Lys Pro Leu Val His
    450                 455                 460

Tyr Asp Leu Ser Gly Pro Arg Gly Lys Phe Asn Lys Phe Lys Leu Pro
465                 470                 475                 480

Val His Val Arg Arg Ser Asn Phe Lys Leu Pro Lys Asn Ser Thr Thr
                485                 490                 495

Pro Val Ile Leu Ile Gly Pro Gly Thr Gly Val Ala Pro Leu Arg Gly
            500                 505                 510

Phe Val Arg Glu Arg Val Gln Gln Val Lys Asn Gly Val Asn Val Gly
            515                 520                 525

Lys Thr Leu Leu Phe Tyr Gly Cys Arg Asn Ser Asn Glu Asp Phe Leu
    530                 535                 540

Tyr Lys Gln Glu Trp Ala Glu Tyr Ala Ser Val Leu Gly Glu Asn Phe
545                 550                 555                 560

Glu Met Phe Asn Ala Phe Ser Arg Gln Asp Pro Ser Lys Lys Val Tyr
                565                 570                 575

Val Gln Asp Lys Ile Leu Glu Asn Ser Gln Leu Val His Glu Leu Leu
            580                 585                 590

Thr Glu Gly Ala Ile Ile Tyr Val Cys Gly Asp Ala Ser Arg Met Ala
            595                 600                 605

Arg Asp Val Gln Thr Thr Ile Ser Lys Ile Val Ala Lys Ser Arg Glu
        610                 615                 620

Ile Ser Glu Asp Lys Ala Ala Glu Leu Val Lys Ser Trp Lys Val Gln
625                 630                 635                 640

Asn Arg Tyr Gln Glu Asp Val Trp
                645
```